(12) United States Patent
Sato et al.

(10) Patent No.: US 6,670,382 B2
(45) Date of Patent: Dec. 30, 2003

(54) HYDROXYFORMAMIDINE DERIVATIVES AND MEDICINES CONTAINING THE SAME

(75) Inventors: Masakazu Sato, Kohnosu (JP); Noriyuki Miyata, Tokyo (JP); Takaaki Ishii, Saitama (JP); Yuko Kobayashi, Saitama (JP); Hideaki Amada, Saitama (JP)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/311,003

(22) PCT Filed: Jun. 15, 2001

(86) PCT No.: PCT/JP01/05108

§ 371 (c)(1),
(2), (4) Date: Dec. 12, 2002

(87) PCT Pub. No.: WO01/96309

PCT Pub. Date: Dec. 20, 2001

(65) Prior Publication Data

US 2003/0186979 A1 Oct. 2, 2003

(30) Foreign Application Priority Data

| Jun. 15, 2000 | (JP) | 2000-180477 |
| Jun. 15, 2000 | (JP) | 2000-180479 |
| Nov. 2, 2000 | (JP) | 2000-336140 |
| Nov. 27, 2000 | (JP) | 2000-359781 |

(51) Int. Cl.[7] .................... C07D 213/53; C07D 401/12; A61K 31/44
(52) U.S. Cl. .................... 514/352; 514/235.5; 514/318; 514/343; 544/124; 546/193; 546/297; 546/276.4
(58) Field of Search .................... 514/352, 235.5, 514/318, 343; 546/297, 193, 276.4; 544/124

(56) References Cited

U.S. PATENT DOCUMENTS

| 3,959,368 A | 5/1976 | DeBaun |
| 3,998,970 A | 12/1976 | DeBaun |
| 4,079,149 A | 3/1978 | Henry |
| 4,474,815 A | 10/1984 | Johnson et al. |
| 5,646,147 A | 7/1997 | Kuhn et al. |

FOREIGN PATENT DOCUMENTS

| DE | 28 06 664 A | 8/1978 |
| DE | 30 05 899 A | 9/1981 |
| EP | 0 004 754 A | 10/1979 |
| EP | 0 009 865 A | 4/1980 |
| EP | 0 015 456 A | 9/1980 |
| EP | 0 024 888 A | 3/1981 |
| EP | 0 052 744 A | 6/1982 |
| EP | 0 094 348 A | 11/1983 |
| EP | 0 207 894 A | 1/1987 |
| JP | 7-505818 | 6/1995 |
| WO | WO 84 01772 A | 5/1984 |
| WO | WO 86 00894 A | 2/1986 |
| WO | WO 93/21157 A2 | 10/1993 |
| WO | WO 94/17748 A1 | 8/1994 |
| WO | WO 01/96309 A1 | 12/2001 |

OTHER PUBLICATIONS

Chemical Abstracts, vol. 109, No. 9, 1988, Columbus, Ohio, US; abstract No. 73101n, T.G. Cullen et al., p. 656; see abstract & ACS Symp Ser. vol. 336, 1987 pp. 173–188 cited in the application.

Chemical Abstracts, vol. 100, No. 15, 1984, Columbus, Ohio, US; abstract No. 120606g, R. Huang, et al., p. 549, see abstract & Daodeng Xuexiao Huaxue Xuebao vol. 4, No. 5, 1983, pp. 589–594.

Chemical Abstracts, vol. 94, No. 23, 1981, Columbus, Ohio, US; abstract No. 191841y, M.J. Bull, et al., p. 613; see abstract & Pestic. Sci., vol. 11, No. 2, 1980 pp. 249–256.

Chemical Abstracts, vol. 51, No. 2, 1957, Columbus, Ohio, US; abstract No. 6603h, G.W. Perold, et al., "Structure of isoxazoline compounds", see abstract & Journal of the American Chemical Society, vol. 79, 1957, Washington, D.C., US, pp. 462–465.

Chemical Abstracts, vol. 109, No. 13, 1988, Columbus, Ohio, US; abstract No., 106489a, J.R. Byberg et al., p. 250; see abstract & J. Comput.–Aided Mol. Des., vol. 1, No. 3, 1987, pp. 181–195.

Chemical Abstracts, vol. 105, No. 15, 1986, Columbus, Ohio, US; abstract No. 129392v, G. Holan, et al., p. 267; see abstract & Spec. Publ.—R. Soc. Chem., vol. 53, 1985, pp. 114–132.

(List continued on next page.)

Primary Examiner—Zinna Northington Davis
(74) Attorney, Agent, or Firm—Sughrue Mion, PLLC

(57) ABSTRACT

Pharmaceutical agents for inhibiting the production of 20-HETE which participates in constriction or dilation of microvessels in major organs such as the kidneys and the cerebral blood vessels, or participates in causing cell proliferation are provided. The present invention relates to hydroxyamidine compounds represented by the formula:

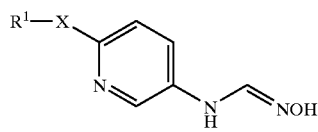

wherein $R^1$ represents a group represented by the formula: $R^2$—$(CH_2)_m$— (wherein $R^2$ represents a $C_{3-8}$ cycloalkyl group, a $C_{2-6}$ alkoxycarbonyl group, a $C_{2-10}$ alkenyl group, a $C_{2-6}$ alkynyl group, a substituted or non-substituted aryl group, or the like, and m is an integer of 1 to 8), a group represented by the formula: $R^3$—A— (wherein $R^3$ represents a hydrogen atom, a $C_{1-6}$ alkoxy group, a $C_{3-8}$ cycloalkoxy group, or the like, and A represents a straight-chain $C_{2-10}$ alkylene group which may be substituted with a $C_{1-6}$ alkyl group or a trifluoromethyl group), or a $C_{3-8}$ cycloalkyl group, and X represents an oxygen atom or a sulfur atom, or pharmaceutically acceptable salts thereof, and relates to medicines including the same as active ingredients.

7 Claims, No Drawings

OTHER PUBLICATIONS

Chemical Abstracts, vol. 102, No. 17, 1985, Columbus, Ohio, US; abstract No. 144795, G. Holan, et al., p. 212; see abstract & Pestic. Sci., vol. 15, No. 6, 1984, pp. 637–641.

Chemical Abstracts, vol. 101, No. 23, 1984, Columbus, Ohio, US; abstract No. 210639v, G. Holan, et al., pp. 607; see abstract & Pestic. Sci., vol. 15, No. 4, 1984, pp. 361–368.

Chemical Abstracts, vol. 98, No. 17, 1983, Columbus, Ohio, US; abstract No. 143124c, pp. 551; see abstract & JP A 57 185 255( . . . ).

Chemical Abstracts, vol. 92, No. 23, 1980, Columbus, Ohio, US; abstract No. 198103b, T. Nishioka, et al., p. 653; see abstract & JPA 54 138 532( . . . ).

Chemical Abstracts, vol. 92, No. 17, 1980, Columbus, Ohio, US, abstract No. 141746j, K. Nanjyo, et al., pp. 155, see abstract & Agric. Biol. Chem., vol. 44, No. 1, 1980, pp. 217–218.

Chemical Abstracts, vol. 90, No. 13, 1979, Columbus, Ohio, US; abstract No. 103840m, S. Tanaka, et al., p. 582; see abstract & JPA 53 116 378 ( . . . ).

Chemical Abstracts, vol. 101, No. 19, 1984, Columbus, Ohio, US; abstract No. 165582h, Y. Katsuda, p. 232; see abstract & JPA 59 110 602 ( . . . ).

Chemical Abstracts, vol. 101, No. 15, 1984, Columbus, Ohio, US: abstract No. 124827y, M.A. Brown, pp. 232; see abstract & Pestic. Biochem. Physiol., vol. 22, No. 1, 1984, pp. 78–85.

Chemical Abstracts, vol. 99, No. 17, 1983, Columbus, Ohio, US; abstract No., 135477a, M.A. Brown, et al., p. 225; see abstract & J. Agric. Food Chem., vol. 31, No. 5, 1983, pp. 1091–1096.

Chemical Abstracts, vol. 95, No. 3, 1981, Columbus, Ohio, US; abstract No. 24511e, p. 644; see abstract JPA 55 115 864 (Kanesho Co).

Chemical Abstracts, vol. 104, No. 1, 1986, Columbus, Ohio, US; abstract No. 2161t, W. Wang, p. 199; see abstract & Kunchong Xuebao, vol. 28, No. 3, 1985, pp. 346–347.

HYDROXYFORMAMIDINE DERIVATIVES AND MEDICINES CONTAINING THE SAME

TECHNICAL FIELD

The present invention relates to hydroxyformamidinopyridine derivatives inhibiting a synthase of 20-hydroxyeicosatetraenoic acid (20-HETE) biosynthesized from arachidonic acid.

BACKGROUND ART

Prostaglandins produced by cyclooxygenase and leucotrienes produced by lipoxygenase have been well known as physiologically active substances synthesized from arachidonic acid. Recently, it has been elucidated that 20-HETE, which is produced from arachidonic acid by the cytochrome P450 family enzymes, functions in various manner in vivo (*J. Vascular Research*, vol. 32, p. 79 (1995)). It has been reported that 20-HETE induces constriction or dilation of microvessels in major organs such as the kidneys and the cerebral blood vessels, and causes cell proliferation, and it is suggested that 20-HETE plays important physiological roles in vivo, and participates in various kidney diseases, cerebrovascular diseases, and circulatory diseases (*J. Vascular Research*, vol. 32, p. 79 (1995); *Am. J. Physiol.*, vol. 277, p. R607 (1999); and the like).

DISCLOSURE OF THE INVENTION

An object of the present invention is to provide a pharmaceutical agent for inhibiting the production of 20-HETE which participates in constriction or dilation of microvessels in major organs such as the kidneys and the cerebral blood vessels, or participates in causing cell proliferation.

As a result of various studies in order to solve the above problem, the present inventors have discovered that aromatic compounds having a specific substructure, and in particular, hydroxyformamidine compounds as pyridine derivatives, unexpectedly possess the inhibitory activity for 20-HETE synthase, to accomplish the present invention.

That is, the present invention relates to a hydroxyformamidine compound represented by the general formula (I) as follows:

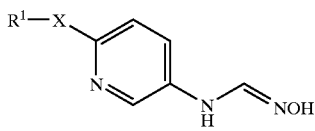

wherein $R^1$ is a group represented by the formula: $R^2$—(CH$_2$)$_m$— (wherein $R^2$ is a $C_{3-8}$ cycloalkyl group, a $C_{2-6}$ alkoxycarbonyl group, a $C_{2-10}$ alkenyl group, a $C_{2-6}$ alkynyl group, a substituted or non-substituted aryl group, a furyl group, an oxolanyl group, a substituted or non-substituted dioxolanyl group, an oxanyl group, a substituted or non-substituted dioxanyl group, a benzodioxanyl group, a piperidyl group, an N—($C_{1-6}$ alkyl)piperidyl group, a substituted or non-substituted pyridyl group, a thienyl group, a substituted or non-substituted thiazolyl group, or a bicyclo[2.2.1]heptanyl group, and m is an integer of 1 to 8), a group represented by the formula: $R^3$—A— (wherein $R^3$ is a hydrogen atom, a $C_{1-6}$ alkoxy group, a $C_{3-8}$ cycloalkoxy group, a di($C_{1-6}$ alkyl)amino group, a substituted or non-substituted arylamino group, a $C_{1-6}$ alkyl (substituted or non-substituted aryl)amino group, a $C_{1-6}$ alkylthio group, a $C_{1-6}$ alkoxy $C_{1-6}$ alkoxy group, a di($C_{1-6}$ alkyl)amino $C_{1-6}$ alkoxy group, a hydroxy group, an acetoxy group, an arylthio group, an aryloxy group, a phthalimidoyl group, a piperidino group, a pyridylthio group, a pyrrolidinyl group, a pyrrolyl group, a morpholino group, or a substituted or non-substituted 2,6-purindion-7-yl group, and A is a straight-chain $C_{2-10}$ alkylene group which may be substituted with a $C_{1-6}$ alkyl group or a trifluoromethyl group), or a $C_{3-8}$ cycloalkyl group, and X is an oxygen atom or a sulfur atom, or a pharmaceutically acceptable salt thereof.

In the compounds of the general formula (I) described above, it is preferable that X is an oxygen atom. In addition, it is more preferable that X is an oxygen atom and $R^1$ is a group represented by the formula: $R^4$—B— (wherein $R^4$ is a di($C_{1-6}$ alkyl)amino group, a di($C_{1-6}$ alkyl)amino $C_{1-6}$ alkoxy group, a piperidino group, a pyrrolidinyl group, or a morpholino group, and B is a straight-chain $C_{2-6}$ alkylene group which may be substituted with one or two methyl groups).

The hydroxyformamidine compounds or pharmaceutically acceptable salts thereof described above are employed in a medicament comprising them as active ingredients. Preferably, they are employed as an inhibitor for production of 20-hydroxyeicosatetraenoic acid (20 HETE), or are employed as a therapeutic agent for kidney diseases, cerebrovascular diseases, or circulatory diseases.

The terms used in the present invention are defined in the following. In the present invention, "$C_{x-y}$" means that the group following the "$C_{x-y}$" has a number of carbon atoms x–y.

The $C_{1-6}$ alkyl group means a straight-chain or branched-chain alkyl group having 1 to 6 carbon atoms. A $C_{1-4}$ alkyl group is preferable. As examples of $C_{1-6}$ alkyl groups, mention may be made of, for example, a methyl group, an ethyl group, a propyl group, an isopropyl group, a n-butyl group, a sec-butyl group, a tert-butyl group, a pentyl group, an isopentyl group, a hexyl group, an isohexyl group, and the like.

The $C_{1-6}$ alkoxy group means a straight-chain or branched-chain alkoxy group having 1 to 6 carbon atoms. A $C_{1-4}$ alkoxy group is preferable. As examples of $C_{1-6}$ alkoxy groups, mention may be made of, for example, a methoxy group, an ethoxy group, a propoxy group, an isopropoxy group, a butoxy group, an isobutoxy group, a tert-butoxy group, a pentyloxy group, an isopentyloxy group, and the like.

The $C_{1-6}$ alkylthio group has a combined structure of a straight-chain or branched-chain alkyl group having 1 to 6 carbon atoms and one thio group (—S—). A $C_{1-4}$ alkylthio group is preferable. As examples of $C_{1-6}$ alkylthio groups, mention may be made of, for example, a methylthio group, an ethylthio group, a propylthio group, and the like.

The $C_{3-8}$ cycloalkyl group refers to a cyclic alkyl group having 3 to 8 carbon atoms, and also includes a group with a structure having bridged ring(s). As examples of $C_{3-8}$ cycloalkoxy groups, mention may be made of, for example, a cyclopropyl group, a cyclobutyl group, a cyclopentyl group, a cyclohexyl group, a cycloheptyl group, and the like.

The $C_{3-8}$ cycloalkoxy group has a combined structure of a cyclic alkyl group having 3 to 8 carbon atoms and one oxy group (—O—). As examples of $C_{3-8}$ cycloalkoxy groups, mention may be made of, for example, a cyclopropyloxy group, a cyclopentyloxy group, a cyclohexyloxy group, a cycloheptyloxy group, and the like.

The di($C_{1-6}$ alkyl)amino group has a structure wherein each of two hydrogen atoms present on the amino group (—NH$_2$) is independently substituted with a straight-chain or branched-chain alkyl group having 1 to 6 carbon atoms. A di(C$_{1-4}$ alkyl)amino group is preferable. As examples of di(C$_{1-6}$ alkyl)amino groups, mention may be made of, for example, an N,N-dimethylamino group, an N,N-diethylamino group, and the like.

The C$_{2-6}$ alkoxycarbonyl group has a combined structure of a straight-chain or branched-chain alkoxy group having 1 to 5 carbon atoms and one carbonyl group (—CO—). A C$_{2-4}$ alkoxycarbonyl group is preferable. As examples of C$_{2-6}$ alkoxycarbonyl groups, mention may be made of, for example, a methoxycarbonyl group, an ethoxycarbonyl group, and the like.

The C$_{1-6}$ alkoxy C$_{1-6}$ alkoxy group has a combined structure of a C$_{1-6}$ alkoxy group and a C$_{1-6}$ alkoxy group. A C$_{1-4}$ alkoxy C$_{1-6}$ alkoxy group is preferable. As examples of C$_{1-6}$ alkoxy C$_{1-6}$ alkoxy groups, mention may be made of, for example, a methoxyethoxy group, an ethoxyethoxy group, and the like.

The di(C$_{1-6}$ alkyl)amino C$_{1-6}$ alkoxy group has a combined structure of a di(C$_{1-6}$ alkyl)amino group and a C$_{1-6}$ alkoxy group. A di(C$_{1-4}$ alkyl)amino C$_{1-4}$ alkoxy group is preferable. As examples of di(C$_{1-6}$ alkyl)amino C$_{1-6}$ alkoxy groups, mention may be made of, for example, an N,N-dimethylaminoethoxy group, an N,N-diethylaminoethoxy group, an N,N-diethylaminoethoxy group, and the like.

The C$_{2-10}$ alkenyl group refers to a straight-chain or branched-chain alkenyl group having at least one double bond and having 2 to 10 carbon atoms. As examples of C$_{2-10}$ alkenyl groups, mention may be made of, for example, an ethenyl group, a 1-propenyl group, a 2-propenyl group, a 2-methyl-1-propenyl group, a 1-butenyl group, a 3-butenyl group, cis-cis- and trans-cis-2,6-dimethyl-1,5-heptadienyl groups, a 2,6-dimethyl-5-heptenyl group, a 1,3-pentadienyl group, a 1,5-dimethyl-4-hexenyl group, and the like.

The C$_{2-6}$ alkynyl group refers to a straight-chain or branched-chain alkynyl group having at least one triple bond and having 2 to 6 carbon atoms. As examples of C$_{2-6}$ alkynyl groups, mention may be made of, for example, an ethynyl group, a 1-propynyl group, a 2-propynyl group, a 2-butynyl group, a 3-butynyl group, and the like.

The bicyclo[2.2.1]heptanyl group corresponds to a bicyclo-type saturated and bridged cyclic hydrocarbon group. As an example thereof, mention may be made of, for example, a bicyclo[2.2.1]hepta-2-yl group, or the like.

The "aryl" refers to a mono-valent group of an aromatic hydrocarbon such as phenyl, naphthyl, or the like. Therefore, in the present invention, the aryl group is a phenyl group, a naphthyl group, or the like, and preferably is a phenyl group. The substituted aryl group means a group wherein at least one hydrogen atom present on the ring thereof is substituted with a C$_{1-6}$ alkyl group, a C$_{1-6}$ alkoxy group, a C$_{2-6}$ alkoxycarbonyl group, an aryl group, an aryloxy group, a phenethyl group, a cyano group, or a halogen atom. As the C$_{1-6}$ alkyl group, the C$_{1-6}$ alkoxy group, and the C$_{2-6}$ alkoxycarbonyl group for the substituents, a C$_{1-4}$ alkyl group, a C$_{1-4}$ alkoxy group, and a C$_{2-4}$ alkoxycarbonyl group are preferable, respectively. In particular, a methyl group, a methoxy group, and a methoxycarbonyl group are preferable, respectively. In addition, as the aryl group and the aryloxy group for the substituents, a phenyl group and a phenoxy group are preferable, respectively. The halogen atom may be a fluorine atom, a chlorine atom, a bromine atom, or an iodine atom, is preferably a fluorine atom, a chlorine atom, or a bromine atom, and is more preferably a fluorine atom or a chlorine atom.

As examples of the substituted aryl groups, mention may be made of a 3-methylphenyl group, a 4-methylphenyl group, a 2,3-dimethoxyphenyl group, a 3,4-dimethoxyphenyl group, a 4-methoxyphenyl group, a 3-methoxyphenyl group, a 2-methoxyphenyl group, a 3-phenoxyphenyl group, a biphenyl group, a 3-bromophenyl group, a 4-bromophenyl group, a 2,5-difluorophenyl group, a 2,4-dichlorophenyl group, a 4-fluorophenyl group, and the like.

The substituted or non-substituted arylamino group has a structure wherein one hydrogen atom of the amino group (—NH$_2$) is substituted with a substituted or non-substituted aryl group. As examples thereof, mention may be made of, for example, a phenylamino group, a 3-methylphenylamino group, and the like.

The C$_{1-6}$ alkyl (substituted or non-substituted aryl)amino group has a structure wherein one hydrogen atom of the amino group (—NH$_2$) is substituted with a straight-chain or branched-chain alkyl group having 1 to 6 carbon atoms, and the other hydrogen atom thereof is substituted with a substituted or non-substituted aryl group. As an example thereof, mention may be made of, for example, an N-ethyl-N-(3-methylphenyl)amino group, or the like.

The arylthio group has a combined structure of an aryl group and one thio group (—S—). As examples thereof, mention may be made of, for example, a phenylthio group, a naphthylthio group, and the like.

The aryloxy group has a combined structure of an aryl group and one oxy group (—O—). As examples thereof, mention may be made of, for example, a phenoxy group, a naphthoxy group, and the like.

The furyl group includes a 2-furyl group or a 3-furyl group.

The oxolanyl group has a structure of a saturated 5-membered ring having one oxygen atom (O) as a hetero atom, and includes a 2-oxolanyl group, or a 3-oxolanyl group.

The dioxolanyl group has a structure of a saturated 5-membered ring having two oxygen atoms (O) as hetero atoms (dioxolane), and preferably refers to a mono-valent group derived by eliminating a hydrogen atom from a 1,3-dioxolane ring. The substituted dioxolanyl group means a group wherein at least one hydrogen atom present on the group described above is substituted with a C$_{1-6}$ alkyl group and preferably a C$_{1-4}$ alkyl group. As an example thereof, a 2,2-dimethyl-1,3-dioxolan-4-yl group or the like may be given.

The oxanyl group has a structure of a saturated 6-membered ring having one oxygen atom (O) as a hetero atom. As examples thereof, mention may be made of, for example, a 2-oxanyl group, a 3-oxanyl group, a 4-oxanyl group, and the like.

The dioxanyl group has a structure of a saturated 6-membered ring having two oxygen atoms (O) as hetero atoms (dioxane). Preferably, it refers to a mono-valent group derived by eliminating a hydrogen atom from a 1,3-dioxane ring. The substituted dioxanyl group means a group wherein at least one hydrogen atom present on the group described above is substituted with a C$_{1-4}$ alkyl group. As an example thereof, a 5,5-dimethyl-1,3-dioxan-2-yl group or the like may be given.

The benzodioxanyl group refers to a mono-valent group derived by eliminating a hydrogen atom from a benzodioxane ring and preferably a 1,4-benzodioxane ring. As an example thereof, a 1,4-benzodioxan-2-yl group or the like may be given.

The phthalimidoyl group refers to a mono-valent group derived by eliminating a hydrogen atom present on the nitrogen atom of phthalimide.

The piperidino group refers to a mono-valent group derived by eliminating a hydrogen atom present on the nitrogen atom of piperidine.

The piperidyl group refers to a mono-valent group derived by eliminating a hydrogen atom present on the carbon atom of piperidine. The N—($C_{1-6}$ alkyl)piperidyl group means a group wherein the nitrogen atom of a piperidyl group is substituted with a $C_{1-6}$ alkyl group. As examples thereof, mention may be made of, for example, a 3-(N-methylpiperidyl) group, a 4-(N-methylpiperidyl) group, and the like.

The pyridyl group includes a 2-pyridyl group, a 3-pyridyl group, or a 4-pyridyl group. In addition, the substituted pyridyl group means a group wherein at least one hydrogen atom present on the ring is substituted with a $C_{1-6}$ alkyl group, preferably a $C_{1-4}$ alkyl group, and more preferably a methyl group. As an example thereof, a 6-methyl-2-pyridyl group or the like may be given.

The pyridylthio group has a combined structure of a pyridyl group and one thio group (—S—). As examples thereof, mention may be made of, for example, a pyridin-2-ylthio group, a pyridin-3-ylthio group, a pyridin-4-ylthio group, and the like. A pyridin-2-ylthio group is preferable.

The pyrrolidinyl group refers to a mono-valent group derived by eliminating a hydrogen atom present on the nitrogen atom or the carbon atom of a pyrrolidine ring. As examples thereof, mention may be made of, for example, a 1-pyrrolidinyl group, a 2-pyrrolidinyl group, a 3-pyrrolidinyl group, and the like. A 1-pyrrolidinyl group is preferable.

The pyrrolyl group includes a 1-pyrrolyl group, a 2-pyrrolyl group, or a 3-pyrrolyl group. A 1-pyrrolyl group (N-pyrrolyl group) is preferable.

The thienyl group includes a 2-thienyl group, or a 3-thienyl group.

The thiazolyl group includes a 2-thiazolyl group, a 4-thiazolyl group, or a 5-thiazolyl group. In addition, the substituted thiazolyl group means a group wherein at least one hydrogen atom present on the ring is substituted with a $C_{1-6}$ alkyl group and preferably a $C_{1-4}$ alkyl group. As an example thereof, a 4-methyl-5-thiazolyl group or the like may be given.

The morpholino group refers to a mono-valent group derived by eliminating a hydrogen atom present on the nitrogen atom of morpholine.

The 2,6-purindion-7-yl group refers to a mono-valent group derived from 2,6-purindione wherein one oxygen atom (=O) is bonded to the carbon atom at the 2-position of the purine ring and one oxygen atom (=O) is bonded to the carbon atom at the 6-position of the purine ring, and refers to a group derived by eliminating a hydrogen atom present on the nitrogen atom at the 7-position. The substituted 2,6-purindion-7-yl means a group wherein at least one of the hydrogen atoms bonded to the nitrogen atom of the group is substituted with a $C_{1-6}$ alkyl group, preferably a $C_{1-4}$ alkyl group, and more preferably a methyl group. As an example thereof, a 1,3-dimethyl-2,6-purindion-7-yl group or the like may be given.

The "straight-chain $C_{2-10}$ alkylene group which may be substituted with a $C_{1-6}$ alkyl group or a trifluoromethyl group" defined in "A" means a straight-chain alkylene group having 2 to 10 carbon atoms, which may be substituted with one or more groups, and preferably one or two groups selected from straight-chain or branched-chain alkyl groups having 1 to 6 carbon atoms and trifluoromethyl groups. Among these, a straight-chain $C_{2-6}$ alkylene group which may be substituted with one or two methyl groups defined in "B" is preferable. As examples thereof, mention may be made of an ethylene group, a 1-methylethylene group, a propylene group, a 2,2-dimethylpropylene group, a butylene group, a 1-methylbutylene group, a hexylene group, a 1-trifluoromethylpropylene group, a heptylene group, a 4-methylpentylene group, a 3-methylbutylene group, a 1-methylpropylene group, a 3-methylpentylene group, a 1,1-dimethylethylene group, and the like. A 2,2-dimethylpropylene group, a hexylene group, and the like are preferable.

In addition, the pharmaceutically acceptable salt refers to a salt with an alkali metal, an alkali earth metal, ammonium, an alkylammonium, or the like, as well as, a salt with a mineral acid or an organic acid. As examples thereof, mention may be made of, for example, a sodium salt, a potassium salt, a calcium salt, an ammonium salt, an aluminum salt, a triethylammonium salt, an acetate, a propionate, a butyrate, a formate, a trifluoroacetate, a maleate, a tartarate, a citrate, a stearate, a succinate, an ethylsuccinate, a lactobionate, a gluconate, a glucoheptonate, a benzoate, a methanesulfonate, an ethanesulfonate, a 2-hydroxyethanesulfonate, a benzenesulfonate, a para-toluenesulfonate, a laurylsulfate, a malate, an aspartate, a glutamate, an adipate, a salt with a cysteine, a salt with an N-acetylcysteine, a hydrochloride, a hydrobromide, a phosphates, a sulfate, a hydroiodide, a nicotinate, an oxalate, a picrate, a thiocyanate, an undecanate, a salt with a polymeric acrylic acid, a salt with a carboxyvinyl polymer, and the like.

The compounds of the present invention can be synthesized according to, for example, the methods described below.

First, a compound represented by the formula (a) described below:

(a)

[wherein Y represents a halogen atom of any one of F, Cl, Br and I] and a compound represented by the formula (b) described below:

R¹XH           (b)

[wherein R¹ and X have the same meanings as described above] are reacted in the presence of an appropriate base to produce a compound represented by the formula (c) described below:

(c)

Subsequently, according to a common method for reducing an aromatic nitro group to an aromatic amino group, the compound represented by the above formula (c) is derived to a compound represented by the formula (d) described below:

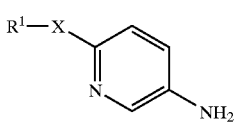

(d)

Subsequently, the compound represented by the above formula (d) is reacted with dimethylformamide dimethylacetal in the presence or absence of an appropriate solvent for 2 to 72 hours at a temperature in the range of room temperature to 150° C., and preferably in the range of 70 to 100° C. to obtain an intermediate. Subsequently, by treating the intermediate, after isolation or in the state as produced, with hydroxylamine or a salt thereof such as a hydrochloride in a solvent such as methanol, the compound of the present invention can be synthesized.

Alternatively, the compound represented by the above formula (d) is reacted with an orthoformate such as trimethyl orthoformate, triethyl orthoformate, or the like in the presence of a catalytic amount of an organic acid such as acetic acid, a mineral acid such as hydrochloric acid, or a salt of a mineral acid and an amine such as pyridine hydrochloride, for 2 to 72 hours at a temperature in the range of room temperature to 150° C., and preferably in the range of 70 to 100° C. to obtain an intermediate. Subsequently, by treating the intermediate, after isolation or in the state as produced, with hydroxylamine in a solvent such as methanol, the compound of the present invention can be synthesized. As described above, the compounds of the present invention can be synthesized from the compounds represented by the above formula (d) using a common method for converting an amino group present on an aromatic ring into an N-hydroxyformamidine group.

The compounds and the pharmaceutically acceptable salts thereof according to the present invention can be administered orally or parenterally, in the form of tablets, capsules, granules, powders, troches, ointments, creams, emulsions, suspensions, suppositories, injectable solutions, or the like, each of which may be produced according to the conventional formulation methods (for example, methods defined in the 12$^{th}$ revision of Japanese Pharmacopeia). These preparation forms may be selected depending on the conditions and ages of the patients, as well as the purpose of the treatment. Upon manufacturing preparations in various formulations, conventional fillers (for example, crystalline cellulose, starch, lactose, mannitol, or the like), binders (for example, hydroxypropylcellulose, polyvinylpyrrolidone, or the like), lubricants (for example, magnesium stearate, talc, or the like), disintegrants (for example, carboxymethylcellulose calcium, or the like), and the like, may be employed.

The dose of the compounds and the pharmaceutically acceptable salts thereof according to the present invention is preferably in the range of 1 to 2000 mg per day in the case of an adult human subject to be treated. They may be administered in a single dose or divided into several doses per day. The doses may appropriately vary depending on the age, weight, and conditions of each individual patient, and the like.

Best Modes for Carrying out the Invention

In the following, the present invention is illustrated in detail with reference to the following examples.

EXAMPLE 1

Synthesis of N-[2-(2-butyn-1-oxy)pyridin-5-yl]-N'-hydroxyformamidine (Compound 65)

Sodium hydride (60% in oil) (0.91 g, 22.7 mmol) was washed with dry hexane, and dimethylformamide (15 ml) and 2-butyn-1-ol (1.59 g, 22.7 mmol) were added thereto. The mixture was stirred for 1 hour at room temperature. The reaction mixture was cooled to 0° C., and a solution of 2-chloro-5-nitropyridine (3 g, 18.9 mmol) in dimethylformamide (20 ml) was added dropwise thereto. The mixture was stirred for 1 hour at room temperature. Water was added to the reaction mixture, followed by extraction with ethyl acetate. The organic layer was dried over MgSO$_4$, and was subsequently concentrated under reduced pressure. Subsequently, iron powders (10.55 g, 189 mmol), isopropanol (10 ml), and a 1N aqueous solution of ammonium chloride (11.3 ml, 11.3 mmol) were added thereto. The mixture was stirred for 1 hour at 85° C. Ethyl acetate (100 ml) was added to the reaction mixture, and insoluble materials were removed therefrom by filtration with a celite. The filtrate was concentrated under reduced pressure, and subsequently a saturated aqueous solution of sodium hydrogencarbonate (20 ml) was added thereto, followed by extraction with ethyl acetate. The organic layer was dried over MgSO$_4$, and was subsequently concentrated under reduced pressure. Subsequently, ethyl orthoformate (6.27 ml) was added thereto, and the mixture was stirred for 16 hours at 100° C. The reaction mixture was concentrated under reduced pressure. Subsequently, a 1N methanol solution of hydroxylamine (22.78 ml) was added thereto, and the mixture was stirred for one hour at room temperature. The reaction mixture was concentrated under reduced pressure to yield a crude product. The crude product was purified by NH type silica gel column chromatography (eluent, hexane:ethyl acetate=1:1), and was subsequently recrystallized from ethyl acetate/hexane to yield the target compound (Compound 65 in Table 1 described below) as of a colorless powder (0.654 g).

Melting point: 155.5 to 157.0° C.

EXAMPLE 2

Synthesis of N-[2-(3-dimethylamino-2,2-dimethylpropyl-1-oxy)pyridin-5-yl]-N'-hydroxyformamidine (Compound 123)

A mixture of 3-dimethylamino-2,2-dimethyl-1-propanol (82.8 g, 630 mml) and 2-chloro-5-nitropyridine (20 g, 126 mmol) was stirred for 6 hours at 100° C. Water was added to the reaction mixture, and the resulting precipitated crystals were obtained by filtration. The precipitate was dried, and methanol (330 ml) and palladium carbon (1.4 g) were added thereto. The mixture was stirred for 2 hours at room temperature. Subsequently, insoluble materials were removed therefrom by filtration with celite. The filtrate was concentrated under reduced pressure. Subsequently, methanol (250 ml) and dimethylformamide dimethylacetal (15.9 g, 133 mmol) were added thereto, and the mixture was stirred under reflux for 3 hours. The reaction mixture was cooled to room temperature. Subsequently, hydroxylamine hydrochloride (9.24 g, 133 mmol) was added thereto, and the mixture was stirred for 2 hours at room temperature. The reaction mixture was concentrated under reduced pressure, and subsequently a saturated aqueous solution of sodium hydrogencarbonate (10 ml) was added thereto, followed by extraction with ethyl acetate. The organic layer was dried over MgSO$_4$, and was subsequently concentrated under reduced pressure. The residue was recrystallized from ethyl acetate/hexane to yield the target compound (Compound 123 in Table 1 described below) as of a colorless powder (19.04 g).

Melting point: 74.0 to 76.5° C.

EXAMPLE 3

Synthesis of N-[2-(pyridin-2-ylmethoxy)pyridin-5-yl]-N'-hydroxyformamidine (Compound 6)

A mixture of 5-amino-2-(pyridin-2-ylmethoxy)pyridine (1.10 g) and ethyl orthoformate (1.782 g) was stirred for 8 hours at 100° C. Subsequently, excess ethyl orthoformate was removed. The residue in methanol (20 ml) was added a 1M methanol solution of hydroxylamine (8.2 ml). The mixture was stirred for 1 hour at room temperature. After removal of the solvent, chloroform was added to the obtained residue. The mixture was washed successively with water and saturated brine, and was subsequently dried over anhydrous sodium sulfate, followed by removal of the solvent. The obtained residue was recrystallized from chloroform to yield the target compound (Compound 6 in Table 1 described below) as of a colorless powder (0.374 g).

Melting point: 153.5 to 155.5° C.

EXAMPLE 4

Synthesis of N-[2-(benzylthio)pyridin-5-yl]-N'-hydroxyformamidine (Compound 104)

A mixture of 5-amino-2-(benzylthio)pyridine (1.11 g) and ethyl orthoformate (1.78 g) was stirred for 8 hours at 100° C. Subsequently, excess ethyl orthoformate was removed. The residue in methanol (20 ml) was added a 1 M methanol solution of hydroxylamine (8.2 ml). The mixture was stirred for 1 hour at room temperature. After removal of the solvent, chloroform was added to the obtained residue. The mixture was washed successively with water and saturated brine, and was subsequently dried over anhydrous sodium sulfate, followed by removal of the solvent. The obtained residue was recrystallized from chloroform to yield the target compound (Compound 104 in Table 1 described below) as of a colorless powder (0.45 g).

Melting point: 133.0 to 135.0° C.

EXAMPLES 5 to 134

In the following, the compounds shown in Table 1 described below were synthesized by carrying out similar reaction procedures to those of Examples 1 to 4 employing the corresponding starting materials.

TABLE 1

| Comp. No. | Chemical Structure | m.p. | M+H (ESI) | M+H (APCI) | M−H (ESI) | M−H (APCI) | Rf Value | TLC* | Eluent | Inhibition (1 M) | IC50 (nM) |
|---|---|---|---|---|---|---|---|---|---|---|---|
| Comp. 1 | piperidine-ethoxy-pyridine formamidoxime | 133.5–135.5 | 264 | | 262 | | 0.11 | SiO2 | AcOEt | 61.0 | 738.4 |
| Comp. 2 | pyrrolidine-ethoxy-pyridine formamidoxime | 130.5–132.5 | 250 | | 248 | | 0.07 | SiO2 | AcOEt | 97.0 | 3095 |
| Comp. 3 | furfuryloxy-pyridine formamidoxime | | 233 | | | | 0.11 | SiO2 | AcOEt | 102.0 | 49.6 |
| Comp. 4 | morpholine-ethoxy-pyridine formamidoxime | 158.5–160.0 | 266 | | 264 | | 0.09 | SiO2 | AcOEt | 99.0 | 339.2 |
| Comp. 5 | pyridyl-ethoxy-pyridine formamidoxime | 128.5–130.0 | | | | | | | | | 14.9 |
| Comp. 6 | pyridylmethoxy-pyridine formamidoxime | 153.5–155.5 | 244 | | | | 0.1 | SiO2 | AcOEt | 65.0 | 514.4 |

TABLE 1-continued

| Comp. No. | Chemical Structure | m.p. | M + H (ESI) | M + H (APCI) | M − H (ESI) | M − H (APCI) | Rf Value | TLC* | Eluent | Inhibition (1 M) | IC50 (nM) |
|---|---|---|---|---|---|---|---|---|---|---|---|
| Comp. 7 | 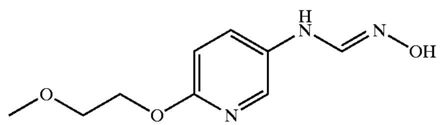 | 104.5–106.0 | | | | | | | | 41.9 | 781.4 |
| Comp. 8 | 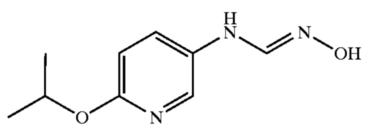 | 116.5–117.0 | | | | | | | | 71.0 | 603.3 |
| Comp. 9 | 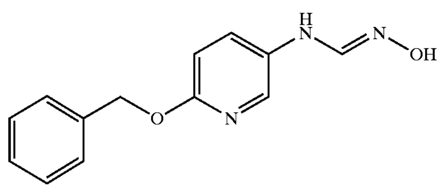 | 163.5–164.0 | | | | | | | | 82.9 | 9.1 |
| Comp. 10 | 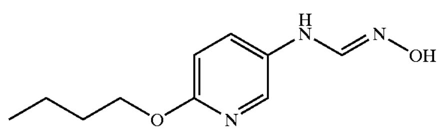 | 127.0–128.0 | | | 247 | | | | | 106.3 | 167.4 |
| Comp. 11 | 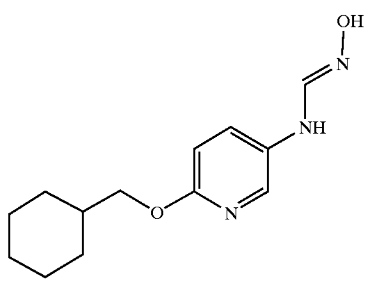 | 156.5–157.0 | 249 | | | | 0.17 | SiO2 | AcOEt | 89.0 | 2.7 |

TABLE 1-continued

| Comp. No. | Chemical Structure | m.p. | M + H (ESI) | M + H (APCI) | M − H (ESI) | M − H (APCI) | Rf Value | TLC* | Eluent | Inhibition (1 M) | IC50 (nM) |
|---|---|---|---|---|---|---|---|---|---|---|---|
| Comp. 12 | 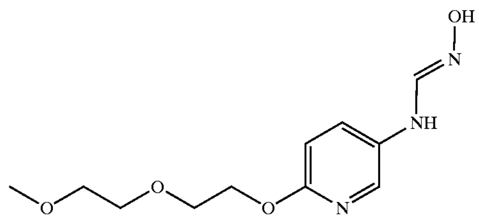 | 90.0–91.5 | 255 | | 253 | | 0.14 | SiO2 | AcOEt | 99.0 | 87.2 |
| Comp. 13 | 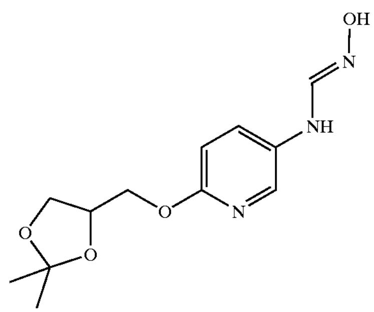 | 97.0–97.5 | 267 | | 265 | | 0.16 | SiO2 | AcOEt | 101.0 | 24.0 |
| Comp. 14 | 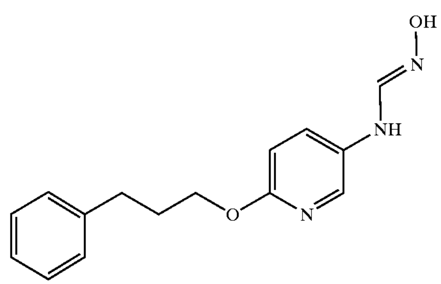 | 125.0–126.0 | 271 | | 269 | | 0.16 | SiO2 | AcOEt | 104.0 | 1.5 |

TABLE 1-continued

| Comp. No. | Chemical Structure | m.p. | M + H (ESI) | M + H (APCI) | M − H (ESI) | M − H (APCI) | Rf Value | TLC* | Eluent | Inhibition (1 μM) | IC50 (nM) |
|---|---|---|---|---|---|---|---|---|---|---|---|
| Comp. 15 | 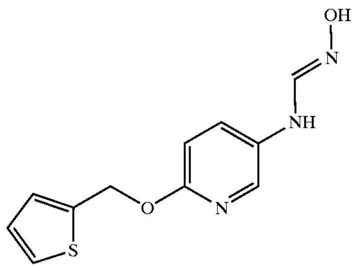 | 159.0–160.0 | 249 | | | | 0.15 | SiO2 | AcOEt | 100.0 | 9.3 |
| Comp. 16 | 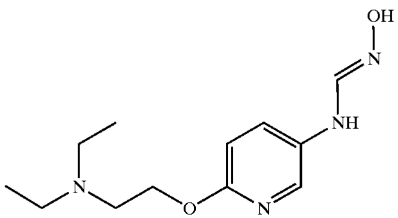 | | 252 | | 250 | | 0.14 | SiO2 | AcOEt | 60.0 | |
| Comp. 17 | 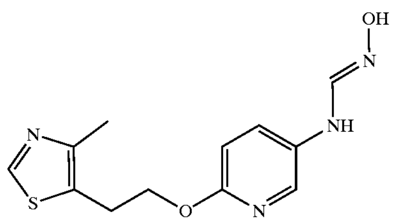 | 159.0–160.0 | 278 | | 276 | | 0.1 | SiO2 | AcOEt | 100.0 | 2.1 |
| Comp. 18 | 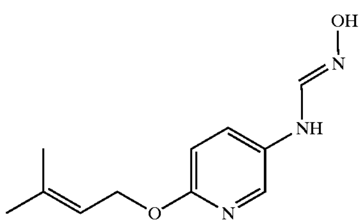 | | 221 | | | | 0.17 | SiO2 | AcOEt | 86.0 | |

TABLE 1-continued

| Comp. No. | Chemical Structure | m.p. | M + H (ESI) | M + H (APCI) | M − H (ESI) | M − H (APCI) | Rf Value | TLC* | Eluent | Inhibition (1 μM) | IC50 (nM) |
|---|---|---|---|---|---|---|---|---|---|---|---|
| Comp. 19 | pyridine with OCH2CH(OiPr) substituent and N-CH=N-OH | | 239 | | 237 | | 0.17 | SiO2 | AcOEt | 104.0 | |
| Comp. 20 | pyridine with O-CH2CH2-C≡CH substituent and N-CH=N-OH | | 205 | | 203 | | 0.17 | SiO2 | AcOEt | 31.0 | |
| Comp. 21 | pyridine with O-CH2-cyclopropyl substituent and N-CH=N-OH | | 207 | | 205 | | 0.15 | SiO2 | AcOEt | 73.0 | |
| Comp. 22 | pyridine with O-CH2CH2-cyclohexyl substituent and N-CH=N-OH | 125.2–126.0 | 263 | | 261 | | 0.17 | SiO2 | AcOEt | 108.0 | 2.1 |

TABLE 1-continued

| Comp. No. | Chemical Structure | m.p. | M + H (ESI) | M + H (APCI) | M − H (ESI) | M − H (APCI) | Rf Value | TLC* | Eluent | Inhibition (1 M) | IC50 (nM) |
|---|---|---|---|---|---|---|---|---|---|---|---|
| Comp. 23 | (structure) | 192.0–192.5 | 244 | | 242 | | 0.09 | SiO2 | AcOEt | 104.0 | 3.9 |
| Comp. 24 | (structure) | | 272 | | 270 | | 0.17 | SiO2 | AcOEt | | |
| Comp. 25 | (structure) | 134.0–135.0 | 290 | | 288 | | 0.13 | SiO2 | AcOEt | 71.0 | 9.6 |

TABLE 1-continued
| Comp. No. | Chemical Structure | m.p. | M+H (ESI) | M+H (APCI) | M−H (ESI) | M−H (APCI) | Rf Value | TLC* | Eluent | Inhibition (1 M) | IC50 (nM) |
|---|---|---|---|---|---|---|---|---|---|---|---|
| Comp. 26 | 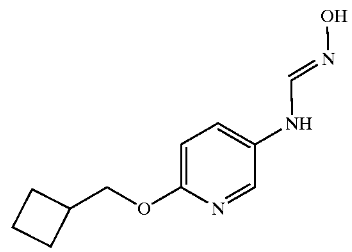 | 136.0–138.0 | 221 | | 219 | | 0.17 | SiO2 | AcOEt | 99.0 | 27.2 |
| Comp. 27 | 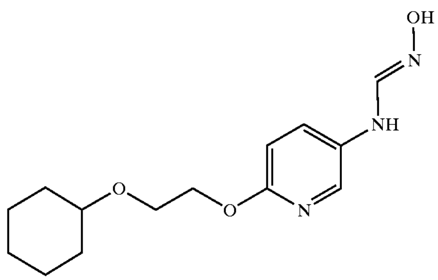 | | 279 | | 277 | | 0.16 | SiO2 | AcOEt | 71.0 | |
| Comp. 28 | 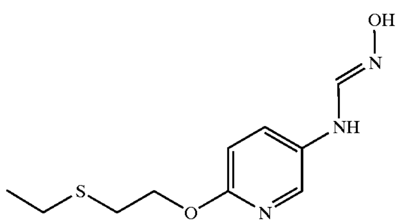 | 104.0–105.0 | 241 | | 239 | | 0.15 | SiO2 | AcOEt | 105.0 | 9.9 |
| Comp. 29 | 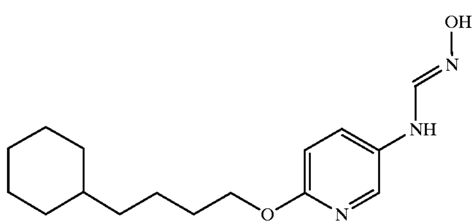 | | 291 | | 289 | | 0.19 | SiO2 | AcOEt | 101.0 | |

TABLE 1-continued

| Comp. No. | Chemical Structure | m.p. | M + H (ESI) | M + H (APCI) | M – H (ESI) | M – H (APCI) | Rf Value | TLC* | Eluent | Inhibition (1 M) | IC50 (nM) |
|---|---|---|---|---|---|---|---|---|---|---|---|
| Comp. 30 | 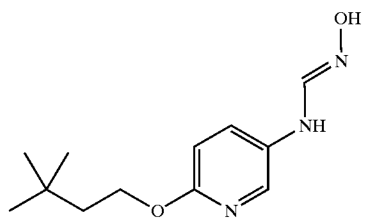 | | 237 | | 235 | | 0.19 | SiO2 | AcOEt | 102.0 | |
| Comp. 31 | 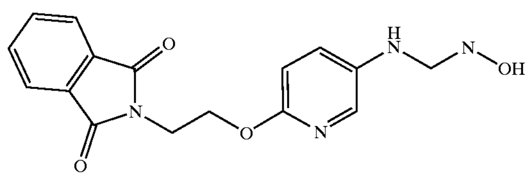 | | 326 | | 324 | | 0.1 | SiO2 | AcOEt | 40.0 | |
| Comp. 32 | 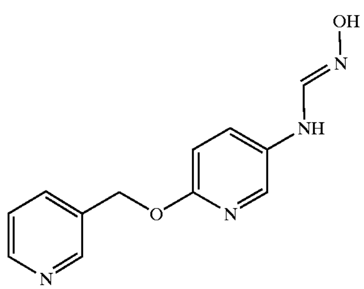 | | 244 | | 242 | | 0.08 | SiO2 | AcOEt | | |
| Comp. 33 | 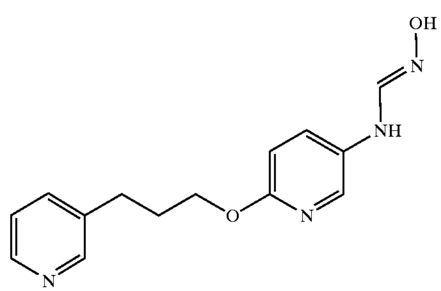 | 122.0–123.0 | 272 | | 270 | | 0.1 | SiO2 | AcOEt | 93.0 | 2.1 |

TABLE 1-continued

| Comp. No. | Chemical Structure | m.p. | M + H (ESI) | M + H (APCI) | M − H (ESI) | M − H (APCI) | Rf Value | TLC* | Eluent | Inhibition (1 M) | IC50 (nM) |
|---|---|---|---|---|---|---|---|---|---|---|---|
| Comp. 34 | 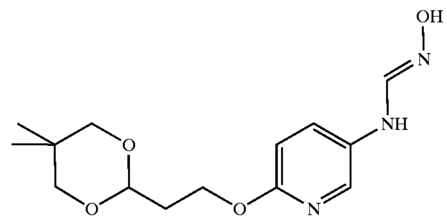 | 107.0–108.0 | 295 | | 293 | | 0.17 | SiO2 | AcOEt | 89.0 | 7.6 |
| Comp. 35 | 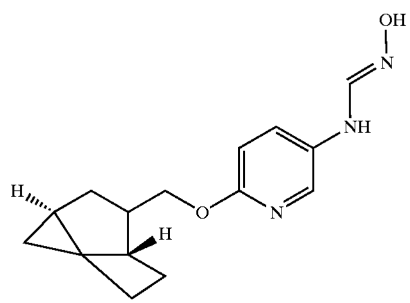 | | 261 | | 259 | | 0.18 | SiO2 | AcOEt | 98.0 | |
| Comp. 36 | 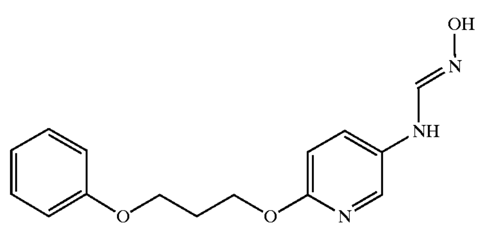 | 145.0–146.0 | 287 | | 285 | | 0.18 | SiO2 | AcOEt | 104.0 | 2.7 |

TABLE 1-continued

| Comp. No. | Chemical Structure | m.p. | M + H (ESI) | M + H (APCI) | M − H (ESI) | M − H (APCI) | Rf Value | TLC* | Eluent | Inhibition (1 M) | IC50 (nM) |
|---|---|---|---|---|---|---|---|---|---|---|---|
| Comp. 37 | (structure) | 181.5–183.5 | 272 | | 270 | | 0.08 | SiO2 | AcOEt | 96.0 | 3.4 |
| Comp. 38 | (structure) | 169.5–170.0 | 249 | | 247 | | 0.16 | SiO2 | AcOEt | 95.0 | 8.5 |
| Comp. 39 | (structure) | | 223 | | 221 | | 0.19 | SiO2 | AcOEt | 62.0 | |

TABLE 1-continued
| Comp. No. | Chemical Structure | m.p. | M + H (ESI) | M + H (APCI) | M − H (ESI) | M − H (APCI) | Rf Value | TLC* | Eluent | Inhibition (1 M) | IC50 (nM) |
|---|---|---|---|---|---|---|---|---|---|---|---|
| Comp. 40 | 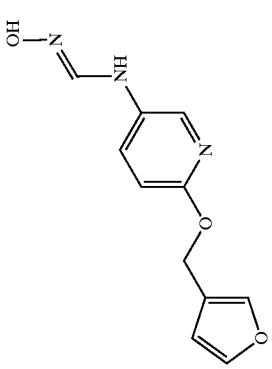 | | 233 | | 231 | | 0.15 | SiO2 | AcOEt | 86.0 | |
| Comp. 41 | 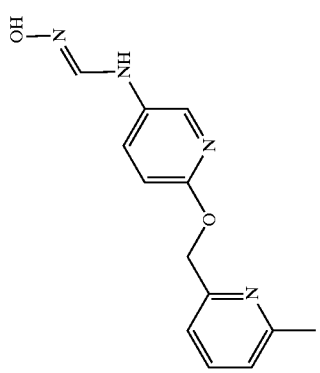 | | 258 | | 256 | | 0.14 | SiO2 | AcOEt | 83.0 | |
| Comp. 42 | 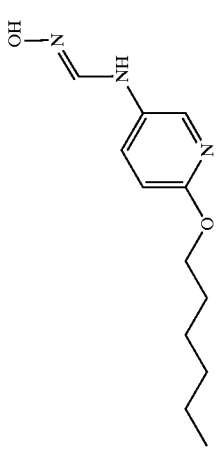 | | 238 | | 236 | | 0.24 | SiO2 | AcOEt | 105.8 | |

TABLE 1-continued

| Comp. No. | Chemical Structure | m.p. | M + H (ESI) | M + H (APCI) | M − H (ESI) | M − H (APCI) | Rf Value | TLC* | Eluent | Inhibition (1 M) | IC50 (nM) |
|---|---|---|---|---|---|---|---|---|---|---|---|
| Comp. 43 | pyridine with O-heptyl chain, CH=N-OH group | | 252 | | 250 | | 0.24 | SiO2 | AcOEt | 89.5 | |
| Comp. 44 | pyridine with O-octyl chain, CH=N-OH group | | 266 | | 264 | | 0.25 | SiO2 | AcOEt | 100.7 | |
| Comp. 45 | pyridine with O-butenyl chain, CH=N-OH group | 143.0–144.5 | 208 | | 206 | | 0.21 | SiO2 | AcOEt | 80.3 | 10.7 |
| Comp. 46 | pyridine with O-butynyl chain, CH=N-OH group | 151.0–152.0 | 220 | | | | 0.20 | SiO2 | AcOEt | 89.9 | 9.8 |

TABLE 1-continued
| Comp. No. | Chemical Structure | m.p. | M + H (ESI) | M + H (APCI) | M − H (ESI) | M − H (APCI) | Rf Value | TLC* | Eluent | Inhibition (1 M) | IC50 (nM) |
|---|---|---|---|---|---|---|---|---|---|---|---|
| Comp. 47 | 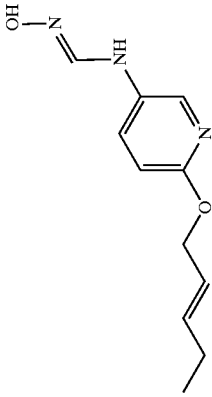 | 82.0–84.0 | 222 | | 220 | | 0.23 | SiO2 | AcOEt | 99.2 | 45.4 |
| Comp. 48 | 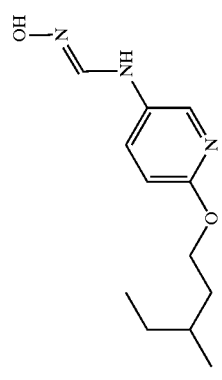 | | 238 | | 236 | | 0.23 | SiO2 | AcOEt | 102.8 | |
| Comp. 49 | 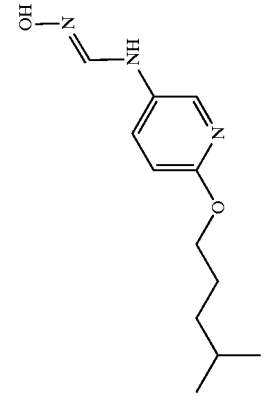 | | 238 | | 236 | | 0.23 | SiO2 | AcOEt | 107.1 | |
| Comp. 50 | 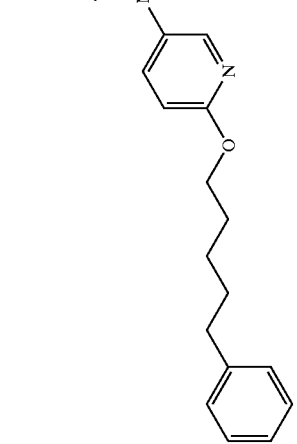 | | 300 | | 298 | | 0.23 | SiO2 | AcOEt | 108.2 | |

TABLE 1-continued

| Comp. No. | Chemical Structure | m.p. | M + H (ESI) | M + H (APCI) | M − H (ESI) | M − H (APCI) | Rf Value | TLC* | Eluent | Inhibition (1 μM) | IC50 (nM) |
|---|---|---|---|---|---|---|---|---|---|---|---|
| Comp. 51 | 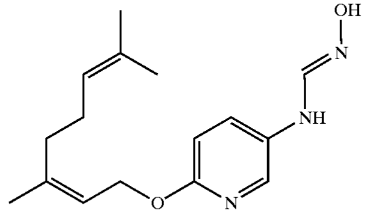 | | | | 288 | | 0.25 | SiO2 | AcOEt | 111.0 | |
| Comp. 52 | 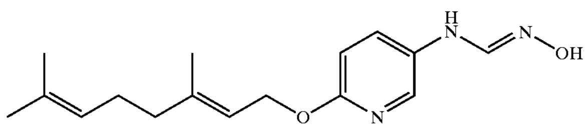 | | | | 288 | | 0.24 | SiO2 | AcOEt | 108.7 | |
| Comp. 53 | 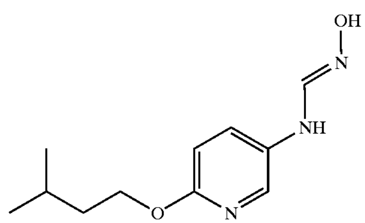 | 123.0–125.0 | 224 | | 222 | | 0.23 | SiO2 | AcOEt | 108.5 | 6.8 |
| Comp. 54 | 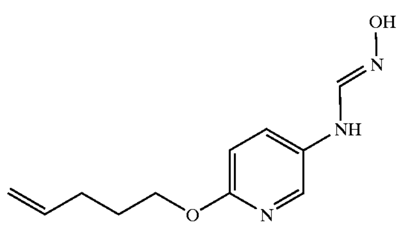 | 120.0–122.0 | 222 | | 220 | | 0.22 | SiO2 | AcOEt | 111.7 | 5.9 |

TABLE 1-continued

| Comp. No. | Chemical Structure | m.p. | M + H (ESI) | M + H (APCI) | M − H (ESI) | M − H (APCI) | Rf Value | TLC* | Eluent | Inhibition (1 M) | IC50 (nM) |
|---|---|---|---|---|---|---|---|---|---|---|---|
| Comp. 55 | 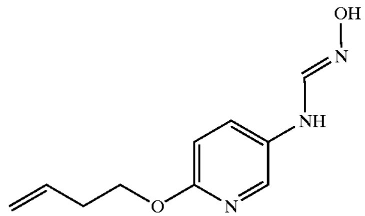 | 119.0–120.0 | 208 | | 206 | | 0.22 | SiO2 | AcOEt | 87.3 | |
| Comp. 56 | 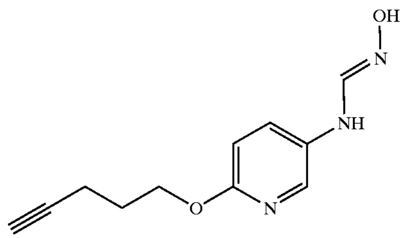 | 124.5–125.5 | 220 | | 218 | | 0.21 | SiO2 | AcOEt | 102.1 | 14.7 |
| Comp. 57 | 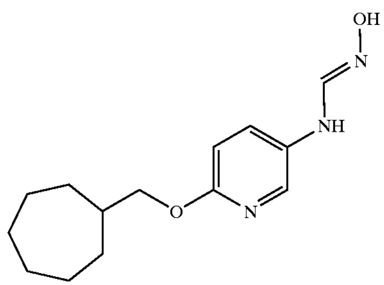 | | 264 | | 262 | | 0.22 | SiO2 | AcOEt | 114.2 | |
| Comp. 58 | 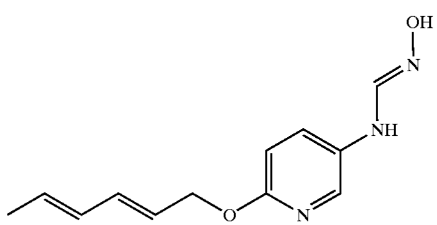 | | 234 | | 232 | | 0.2 | SiO2 | AcOEt | 106.6 | |

TABLE 1-continued

| Comp. No. | Chemical Structure | m.p. | M + H (ESI) | M + H (APCI) | M − H (ESI) | M − H (APCI) | Rf Value | TLC* | Eluent | Inhibition (1 M) | IC50 (nM) |
|---|---|---|---|---|---|---|---|---|---|---|---|
| Comp. 59 | 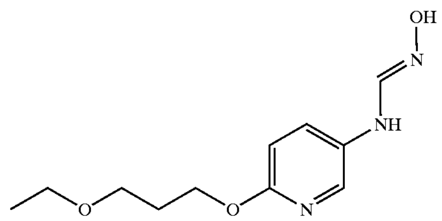 | 99.0–100.0 | 240 | | 238 | | 0.20 | SiO2 | AcOEt | 109.6 | 4.4 |
| Comp. 60 | 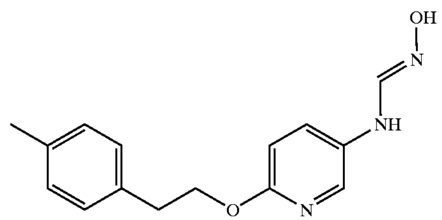 | | 272 | | 270 | | 0.21 | SiO2 | AcOEt | 109.9 | |
| Comp. 61 | 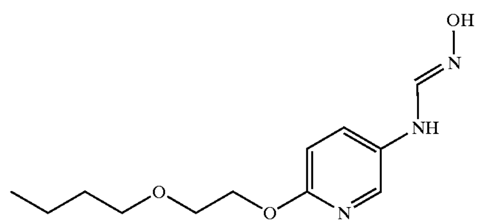 | 113.0–114.5 | 254 | | 252 | | 0.21 | SiO2 | AcOEt | 99.8 | 13.1 |
| Comp. 62 | 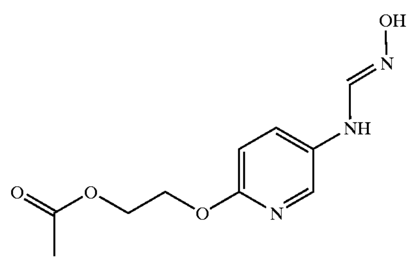 | | 240 | | 238 | | 0.18 | SiO2 | AcOEt | 112.8 | |

TABLE 1-continued

| Comp. No. | Chemical Structure | m.p. | M + H (ESI) | M + H (APCI) | M − H (ESI) | M − H (APCI) | Rf Value | TLC* | Eluent | Inhibition (1 M) | IC50 (nM) |
|---|---|---|---|---|---|---|---|---|---|---|---|
| Comp. 63 | 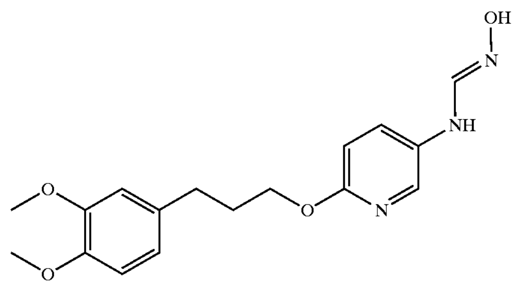 | | 332 | | 330 | | 0.17 | SiO2 | AcOEt | 102.3 | |
| Comp. 64 | 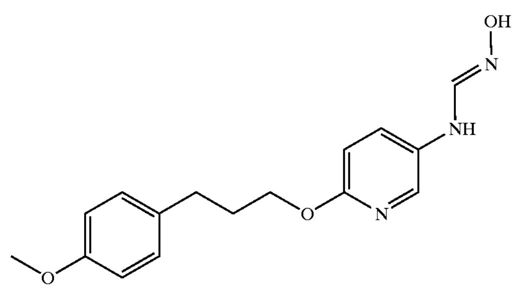 | | 302 | | 300 | | 0.21 | SiO2 | AcOEt | 100.7 | |
| Comp. 65 | 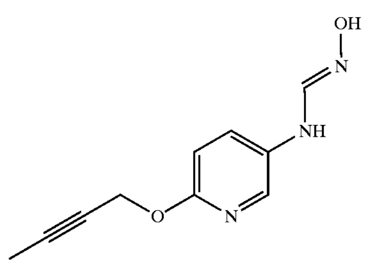 | 155.5–157.0 | 206 | | | | 0.21 | SiO2 | AcOEt | 86.9 | 68.2 |

TABLE 1-continued

| Comp. No. | Chemical Structure | m.p. | M+H (ESI) | M+H (APCI) | M−H (ESI) | M−H (APCI) | Rf Value | TLC* | Eluent | Inhibition (1 M) | IC50 (nM) |
|---|---|---|---|---|---|---|---|---|---|---|---|
| Comp. 66 | (3-bromophenethyloxy pyridine hydroxyiminomethyl amine) | | 337 | | 335 | | 0.20 | SiO2 | AcOEt | 105.3 | |
| Comp. 67 | (4-bromophenethyloxy pyridine hydroxyiminomethyl amine) | | 337 | | 335 | | 0.20 | SiO2 | AcOEt | 108.6 | |
| Comp. 68 | (ethyl ester alkyloxy pyridine hydroxyiminomethyl amine) | | 296 | | 294 | | 0.20 | SiO2 | AcOEt | 102.6 | |
| Comp. 69 | (2-methoxyphenethyloxy pyridine hydroxyiminomethyl amine) | 159.5–161.0 | 288 | | 286 | | 0.18 | SiO2 | AcOEt | 102.8 | 6.5 |

TABLE 1-continued

| Comp. No. | Chemical Structure | m.p. | M + H (ESI) | M + H (APCI) | M − H (ESI) | M − H (APCI) | Rf Value | TLC* | Eluent | Inhibition (1 M) | IC50 (nM) |
|---|---|---|---|---|---|---|---|---|---|---|---|
| Comp. 70 | 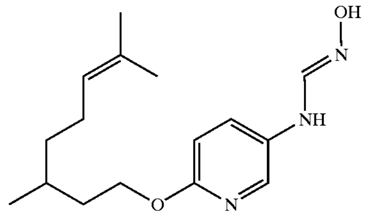 | | 292 | | 290 | | 0.24 | SiO2 | AcOEt | 108.1 | |
| Comp. 71 | 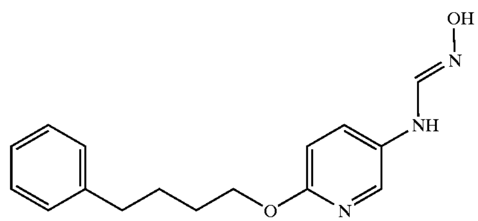 | | 286 | | 284 | | 0.20 | SiO2 | AcOEt | 99.0 | |
| Comp. 72 | 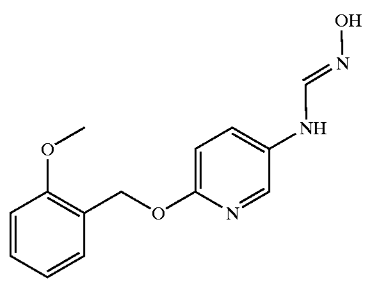 | 146.5–147.5 | 274 | | 272 | | 0.18 | SiO2 | AcOEt | 92.9 | 59.0 |

TABLE 1-continued

| Comp. No. | Chemical Structure | m.p. | M+H (ESI) | M+H (APCI) | M−H (ESI) | M−H (APCI) | Rf Value | TLC* | Eluent | Inhibition (1 μM) | IC50 (nM) |
|---|---|---|---|---|---|---|---|---|---|---|---|
| Comp. 73 | (2,5-difluorobenzyloxy pyridine oxime) | 158.5–159.5 | 280 | | 278 | | 0.23 | SiO2 | AcOEt | 105.0 | 6.4 |
| Comp. 74 | (2,4-dichlorobenzyloxy pyridine oxime) | | 313 | | 311 | | 0.20 | SiO2 | AcOEt | 69.3 | |
| Comp. 75 | (2-phenethylbenzyloxy pyridine oxime) | | 348 | | 346 | | 0.21 | SiO2 | AcOEt | 88.5 | |

TABLE 1-continued

| Comp. No. | Chemical Structure | m.p. | M + H (ESI) | M + H (APCI) | M − H (ESI) | M − H (APCI) | Rf Value | TLC* | Eluent | Inhibition (1 M) | IC50 (nM) |
|---|---|---|---|---|---|---|---|---|---|---|---|
| Comp. 76 | (structure) | | 336 | | 334 | | 0.20 | SiO2 | AcOEt | 100.2 | |
| Comp. 77 | (structure) | 164.5–165.5 | 274 | | 272 | | 0.20 | SiO2 | AcOEt | 100.3 | 3.3 |
| Comp. 78 | (structure) | 126.0–127.0 | 274 | | 272 | | 0.21 | SiO2 | AcOEt | 100.2 | 4.2 |

TABLE 1-continued
| Comp. No. | Chemical Structure | m.p. | M + H (ESI) | M + H (APCI) | M − H (ESI) | M − H (APCI) | Rf Value | TLC* | Eluent | Inhibition (1 M) | IC50 (nM) |
|---|---|---|---|---|---|---|---|---|---|---|---|
| Comp. 79 | 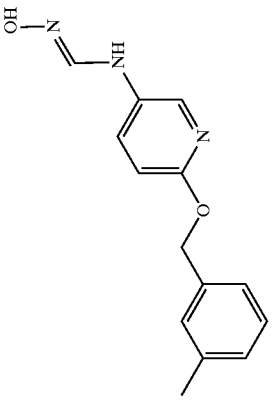 | | 258 | | 256 | | 0.21 | SiO2 | AcOEt | 100.6 | |
| Comp. 80 | 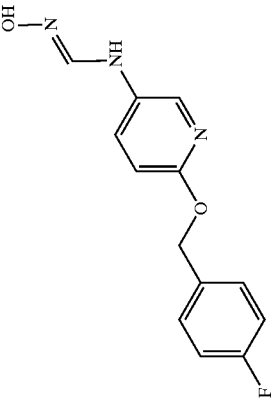 | 166.5–167.5 | 262 | | 260 | | 0.21 | SiO2 | AcOEt | 102.9 | 3.9 |
| Comp. 81 | 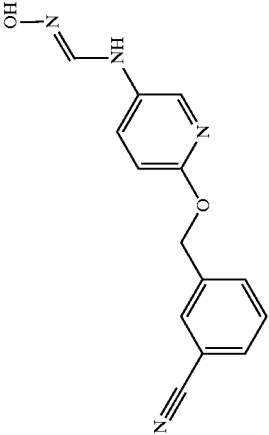 | 166.5–167.0 | 269 | | | | 0.19 | SiO2 | AcOEt | 104.4 | 1.7 |

TABLE 1-continued

| Comp. No. | Chemical Structure | m.p. | M + H (ESI) | M + H (APCI) | M − H (ESI) | M − H (APCI) | Rf Value | TLC* | Eluent | Inhibition (1 M) | IC50 (nM) |
|---|---|---|---|---|---|---|---|---|---|---|---|
| Comp. 82 | 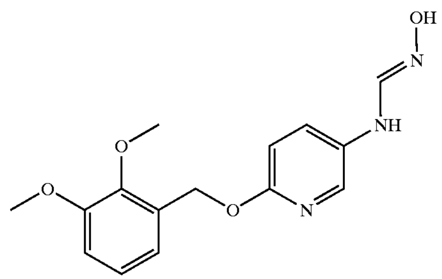 | 128.5–129.0 | 304 | | | | 0.18 | SiO2 | AcOEt | 104.5 | 60.1 |
| Comp. 83 | 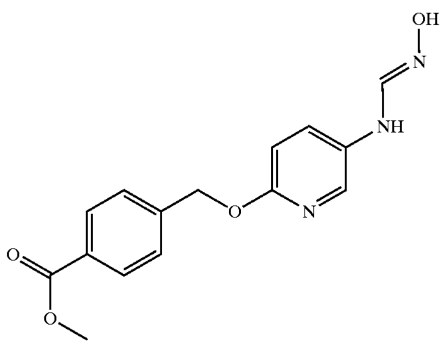 | | 302 | | 318 | | 0.17 | SiO2 | AcOEt | 98.8 | |
| Comp. 84 | 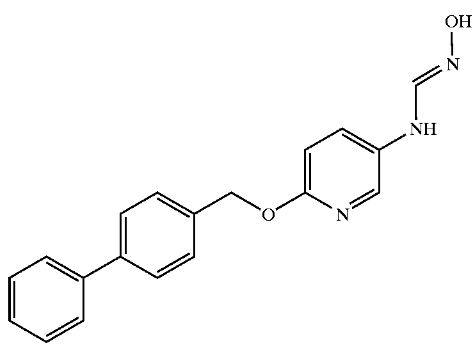 | | 320 | | | | 0.19 | SiO2 | AcOEt | 105.3 | |

TABLE 1-continued
| Comp. No. | Chemical Structure | m.p. | M + H (ESI) | M + H (APCI) | M − H (ESI) | M − H (APCI) | Rf Value | TLC* | Eluent | Inhibition (1 M) | IC50 (nM) |
|---|---|---|---|---|---|---|---|---|---|---|---|
| Comp. 85 | 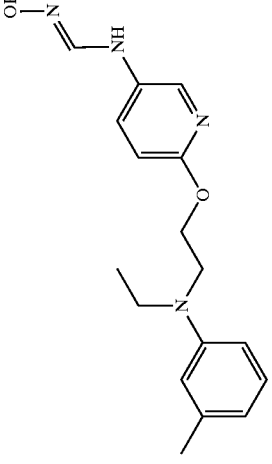 | | 315 | | 313 | | 0.22 | SiO2 | AcOEt | 100.8 | |
| Comp. 86 | 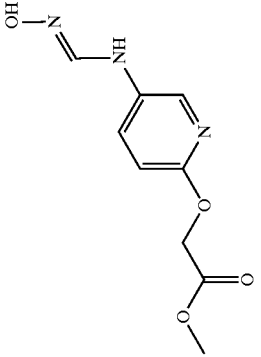 | | 226 | | 224 | | 0.20 | SiO2 | AcOEt | 82.6 | |
| Comp. 87 | 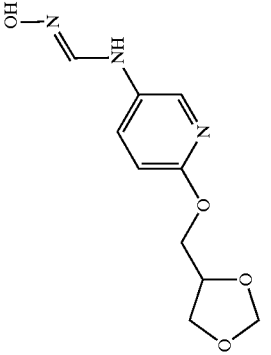 | 186.5–187.0 | 240 | | 238 | | 0.19 | SiO2 | AcOEt | 87.0 | 264.3 |

TABLE 1-continued

| Comp. No. | Chemical Structure | m.p. | M + H (ESI) | M + H (APCI) | M − H (ESI) | M − H (APCI) | Rf Value | TLC* | Eluent | Inhibition (1 μM) | IC50 (nM) |
|---|---|---|---|---|---|---|---|---|---|---|---|
| Comp. 88 | 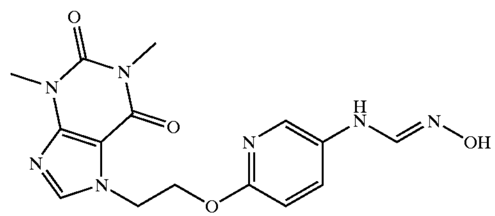 | | 360 | | 358 | | 0.16 | SiO2 | AcOEt | 71.8 | |
| Comp. 89 | 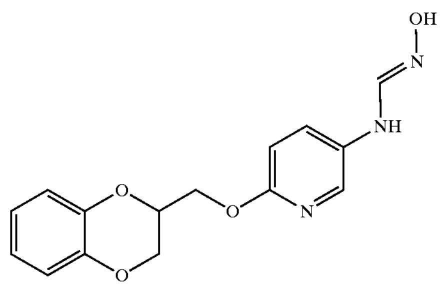 | | 302 | | 300 | | 0.20 | SiO2 | AcOEt | | |
| Comp. 90 | 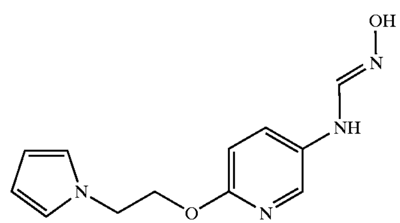 | 186.5–167.0 | 247 | | 245 | | 0.17 | SiO2 | AcOEt | 105.7 | 4.3 |
| Comp. 91 | 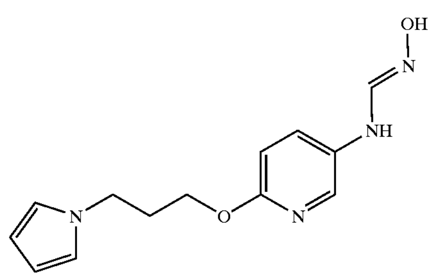 | 140.0–141.0 | 261 | | 259 | | 0.19 | SiO2 | AcOEt | 103.0 | 6.4 |

TABLE 1-continued

| Comp. No. | Chemical Structure | m.p. | M + H (ESI) | M + H (APCI) | M − H (ESI) | M − H (APCI) | Rf Value | TLC* | Eluent | Inhibition (1 M) | IC50 (nM) |
|---|---|---|---|---|---|---|---|---|---|---|---|
| Comp. 92 | (structure) | 111.5–112.0 | 228 | | 226 | | 0.21 | SiO2 | AcOEt | 87.6 | 71.9 |
| Comp. 93 | (structure) | 109.0–111.0 | 242 | | 240 | | 0.21 | SiO2 | AcOEt | 97.4 | 6.6 |
| Comp. 94 | (structure) | 153.0–154.0 | 274 | | 272 | | 0.21 | SiO2 | AcOEt | 100.3 | 3.2 |
| Comp. 95 | (structure) | | 290 | | 288 | | 0.21 | SiO2 | AcOEt | 96.5 | |

TABLE 1-continued

| Comp. No. | Chemical Structure | m.p. | M+H (ESI) | M+H (APCI) | M−H (ESI) | M−H (APCI) | Rf Value | TLC* | Eluent | Inhibition (1 M) | IC50 (nM) |
|---|---|---|---|---|---|---|---|---|---|---|---|
| Comp. 96 | 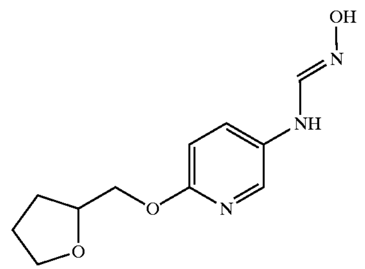 | 114.0–115.0 | 238 | | 236 | | 0.18 | SiO2 | AcOEt | 92.3 | 139.7 |
| Comp. 97 | 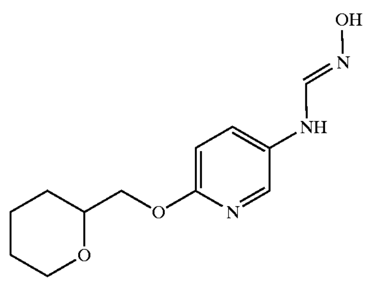 | 149.5–152.5 | 252 | | 250 | | 0.19 | SiO2 | AcOEt | 85.5 | 58.1 |
| Comp. 98 | 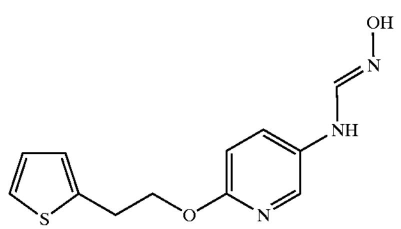 | 137.5–138.5 | 264 | | 262 | | 0.20 | SiO2 | AcOEt | 100.7 | 4.3 |

TABLE 1-continued
| Comp. No. | Chemical Structure | m.p. | M+H (ESI) | M+H (APCI) | M−H (ESI) | M−H (APCI) | Rf Value | TLC* | Eluent | Inhibition (1 M) | IC50 (nM) |
|---|---|---|---|---|---|---|---|---|---|---|---|
| Comp. 99 | 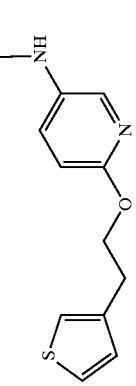 | 138.0–140.0 | 264 | | 262 | | 0.21 | SiO2 | AcOEt | 95.4 | 1.9 |
| Comp. 100 | 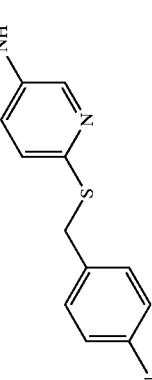 | | | 294 | 292 | 292 | 0.30 | SiO2 (NH) | AcOEt | 79.5 | |
| Comp. 101 | 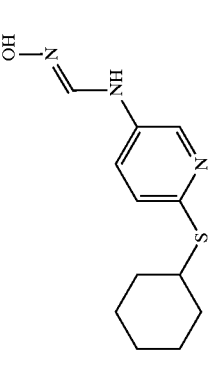 | | 252 | 252 | 250 | 250 | 0.30 | SiO2 (NH) | AcOEt | 91.8 | |
| Comp. 102 | 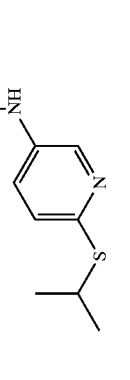 | 141.0–142.0 | 212 | 212 | 210 | 210 | 0.32 | SiO2 (NH) | AcOEt | 74.5 | 18.2 |

TABLE 1-continued

| Comp. No. | Chemical Structure | m.p. | M+H (ESI) | M+H (APCI) | M−H (ESI) | M−H (APCI) | Rf Value | TLC* | Eluent | Inhibition (1 M) | IC50 (nM) |
|---|---|---|---|---|---|---|---|---|---|---|---|
| Comp. 103 | ![structure] | | | 256 | 254 | 254 | 0.28 | SiO2 (NH) | AcOEt | 79.9 | |
| Comp. 104 | ![structure] | 133.0–135.0 | | 260 | 258 | 258 | 0.28 | SiO2 (NH) | AcOEt | 103.6 | |
| Comp. 105 | ![structure] | | 226 | 226 | 224 | 224 | 0.32 | SiO2 (NH) | AcOEt | 100.5 | |
| Comp. 106 | ![structure] | | 240 | 240 | 238 | 238 | 0.35 | SiO2 (NH) | AcOEt | 77.5 | |

TABLE 1-continued

| Comp. No. | Chemical Structure | m.p. | M+H (ESI) | M+H (APCI) | M−H (ESI) | M−H (APCI) | Rf Value | TLC* | Eluent | Inhibition (1 M) | IC50 (nM) |
|---|---|---|---|---|---|---|---|---|---|---|---|
| Comp. 107 | 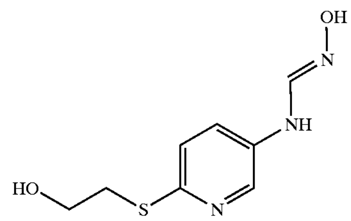 | 115.0–115.5 | 214 | 214 | 212 | 212 | 0.10 | SiO2 (NH) | AcOEt | 83.1 | 294.3 |
| Comp. 108 | 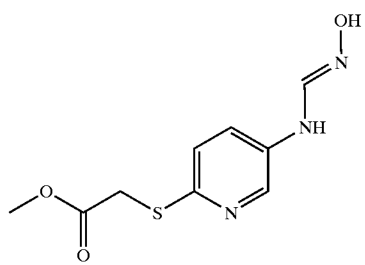 | | 238 | 242 | 240 | 240 | 0.25 | SiO2 (NH) | AcOEt | 89.7 | |
| Comp. 109 | 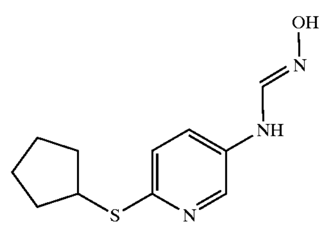 | 153.5–154.5 | 238 | 238 | 236 | 236 | 0.30 | SiO2 (NH) | AcOEt | 82.1 | 11.5 |
| Comp. 110 | 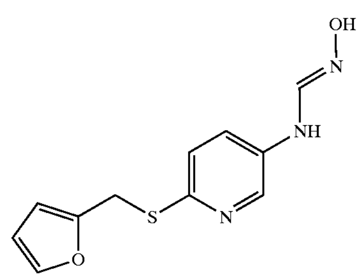 | 140.5–141.5 | 250 | 250 | 248 | 248 | 0.30 | SiO2 (NH) | AcOEt | 85.7 | 12.1 |

TABLE 1-continued
| Comp. No. | Chemical Structure | m.p. | M+H (ESI) | M+H (APCI) | M−H (ESI) | M−H (APCI) | Rf Value | TLC* | Eluent | Inhibition (1 M) | IC50 (nM) |
|---|---|---|---|---|---|---|---|---|---|---|---|
| Comp. 111 | 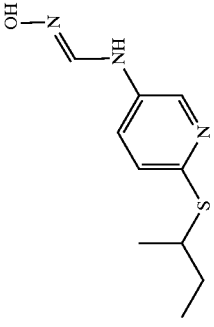 | 125.5–127.5 | 226 | 226 | 224 | 224 | 0.35 | SiO2 (NH) | AcOEt | 76.8 | 33.8 |
| Comp. 112 | 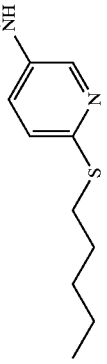 | | 240 | 240 | 238 | 238 | 0.35 | SiO2 (NH) | AcOEt | 101.5 | |
| Comp. 113 | 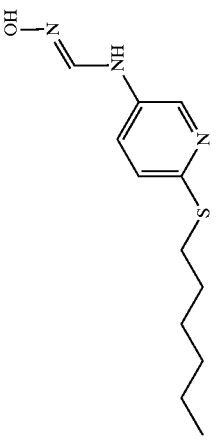 | | 254 | 254 | 252 | 252 | 0.38 | SiO2 (NH) | AcOEt | 81.3 | |
| Comp. 114 | 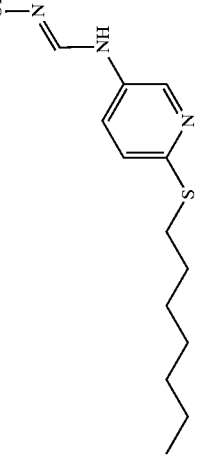 | | | 268 | 266 | 266 | 0.38 | SiO2 (NH) | AcOEt | 85.1 | |

TABLE 1-continued

| Comp. No. | Chemical Structure | m.p. | M+H (ESI) | M+H (APCI) | M−H (ESI) | M−H (APCI) | Rf Value | TLC* | Eluent | Inhibition (1 M) | IC50 (nM) |
|---|---|---|---|---|---|---|---|---|---|---|---|
| Comp. 115 | 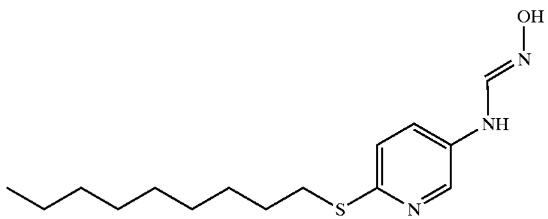 | | | 296 | 294 | 294 | 0.38 | SiO2 (NH) | AcOEt | 89.0 | |
| Comp. 116 | 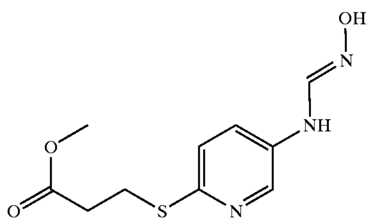 | | 256 | 256 | | | 0.30 | SiO2 (NH) | AcOEt | 93.1 | |
| Comp. 117 | 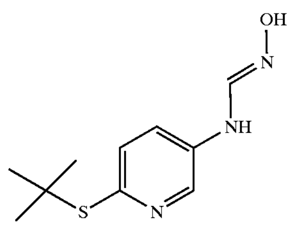 | 174.5–175.0 | | 226 | 224 | 224 | 0.30 | SiO2 (NH) | AcOEt | 69.3 | |
| Comp. 118 | 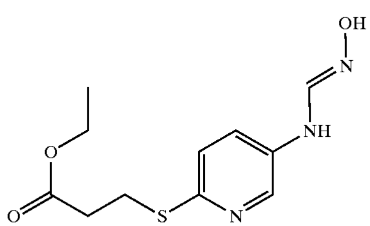 | | | 270 | 268 | 268 | 0.32 | SiO2 (NH) | AcOEt | 100.7 | 435.4 |

TABLE 1-continued

| Comp. No. | Chemical Structure | m.p. | M + H (ESI) | M + H (APCI) | M − H (ESI) | M − H (APCI) | Rf Value | TLC* | Eluent | Inhibition (1 M) | IC50 (nM) |
|---|---|---|---|---|---|---|---|---|---|---|---|
| Comp. 119 | 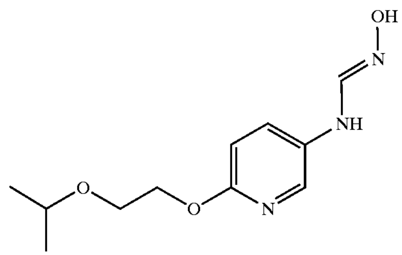 | | 274 | 274 | 272 | 272 | 0.32 | SiO2 (NH) | AcOEt | 116.1 | 116.7 |
| Comp. 120 | 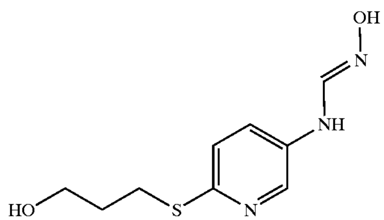 | 105.0–105.5 | 228 | 228 | 226 | 226 | 0.13 | SiO2 (NH) | AcOEt | 102.0 | 400.4 |
| Comp. 121 | 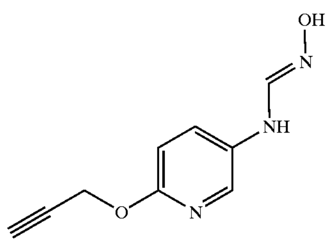 | 143.5–144.5 | 192 | | | | 0.20 | SiO2 (NH) | AcOEt | 99.8 | |
| Comp. 122 | 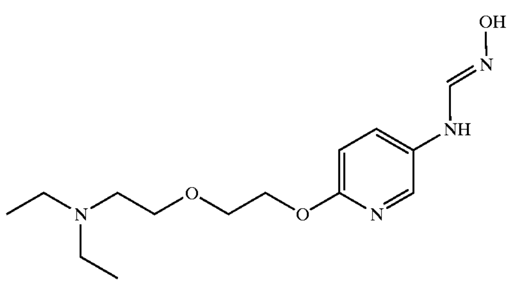 | | | | | 295 | | | | 99.6 | 623.7 |

TABLE 1-continued

| Comp. No. | Chemical Structure | m.p. | M + H (ESI) | M + H (APCI) | M − H (ESI) | M − H (APCI) | Rf Value | TLC* | Eluent | Inhibition (1 M) | IC50 (nM) |
|---|---|---|---|---|---|---|---|---|---|---|---|
| Comp. 123 | 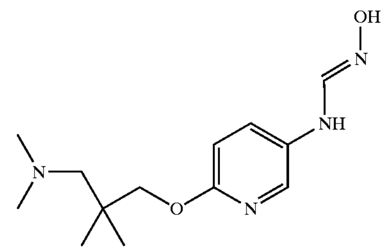 | 74.0–76.5 | | | | | | | | 97.5 | 0.6 |
| Comp. 124 | 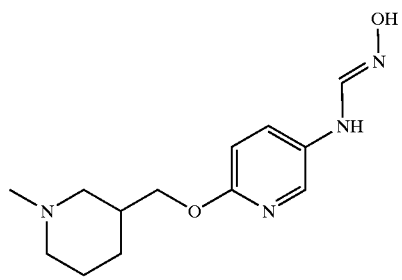 | 122.0–124.0 | | | | | | | | 92.6 | 141.6 |
| Comp. 125 | 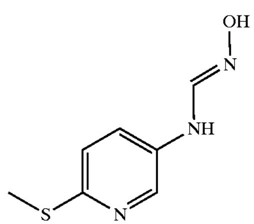 | | | 184 | | 182 | 0.28 | SiO2 (NH) | AcOEt | | |
| Comp. 126 | 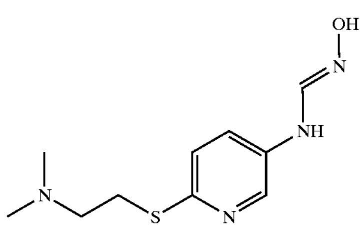 | 153.5–154.5 | | | | | | | | | |

TABLE 1-continued

| Comp. No. | Chemical Structure | m.p. | M+H (ESI) | M+H (APCI) | M−H (ESI) | M−H (APCI) | Rf Value | TLC* | Eluent | Inhibition (1 M) | IC50 (nM) |
|---|---|---|---|---|---|---|---|---|---|---|---|
| Comp. 127 | 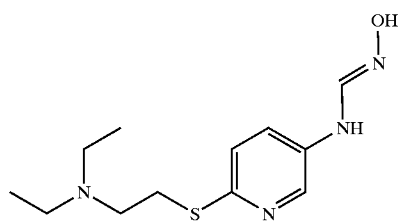 | 124.5–125.5 | | | | | | | | | 329.6 |
| Comp. 128 | 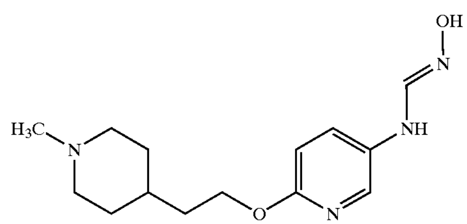 | 131.0–133.0 | 279 | | 277 | | 0.14 | SiO2 (NH) | AcOEt | | 311.6 |
| Comp. 129 | 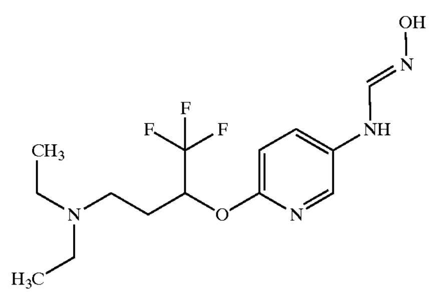 | 109.0–111.0 | 335 | | 333 | | 0.34 | SiO2 (NH) | AcOEt | | |
| Comp. 130 | 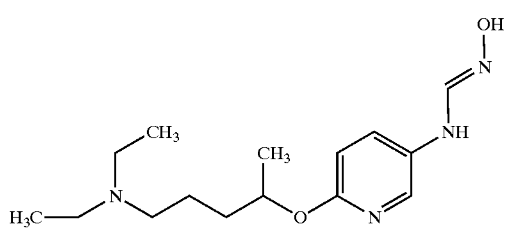 | 122 (dec.) | 295 | | 293 | | 0.32 | SiO2 (NH) | AcOEt | | |

TABLE 1-continued

| Comp. No. | Chemical Structure | m.p. | M+H (ESI) | M+H (APCI) | M−H (ESI) | M−H (APCI) | Rf Value | TLC* | Eluent | Inhibition (1 M) | IC50 (nM) |
|---|---|---|---|---|---|---|---|---|---|---|---|
| Comp. 131 | 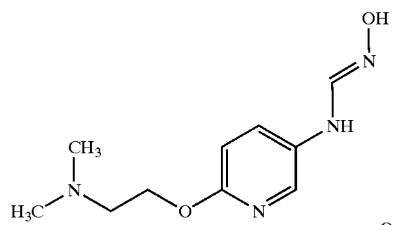 | 105.0–106.0 | 225 | | 223 | | 0.11 | SiO2 (NH) | AcOEt | | |
| Comp. 132 | 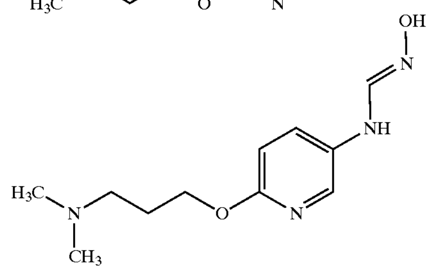 | 108.0–112.0 | 239 | | 237 | | 0.11 | SiO2 (NH) | AcOEt | | 566.2 |
| Comp. 133 | 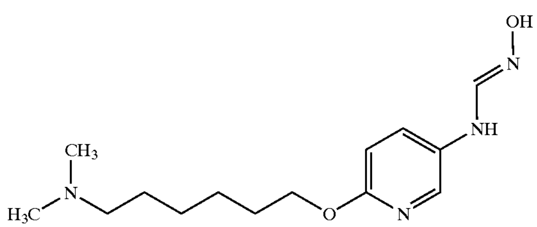 | 110.0–111.5 | 281 | | 279 | | 0.06 | SiO2 (NH) | Hex:AcOEt = 1:1 | | 53.6 |
| Comp. 134 | 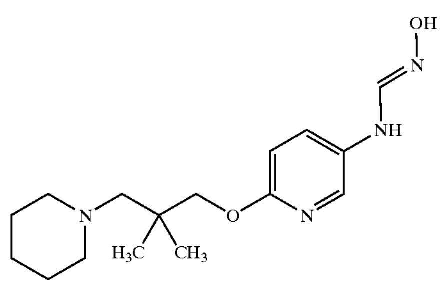 | 91.0–93.0 | 307 | | 305 | | 0.29 | SiO2 (NH) | AcOEt | | |

*SiO2: Merck pre-coated plates Silica gel 60 F254, SiO2(NH): TLC plate NH Fuji Silysia Chemical LTD.

Experimental Example
[Inhibitory Effect of 20-HETE Synthase Derived from Rat Kidney Microsome]

Regarding the compounds listed in the Table described above, their inhibitory activities on production of 20-HETE were examined.

This examination was carried out based on the method described in *J. Pharmacol. Exp. Ther.*, Vol. 268, p. 474 (1994).

The subject compound in an amount of 1 μM was added to a 50 mM of 3-morpholinopropanesulfonic acid buffer (MOPS) (pH 7.4), containing 5 mM of magnesium chloride, and 1 mM of ethylenediaminetetraacetic acid (EDTA) disodium salt.

Subsequently, the rat kidney microsome fraction prepared from the kidney of a spontaneously hypertensive rat (male, 6 weeks of age) as an enzyme, [5,6,8,9,11,12,14,15] tritium-arachidonic acid (supplied by Amasham) as a substrate, and NADPH (supplied by Sigma) as a coenzyme were added, and were reacted for 1.5 hours at 37° C.

After the reaction was quenched by adding formic acid (supplied by Wako Pure Chemical Industries Ltd.) to the reaction solution, acetonitrile (final concentration of 50%) was added thereto, and the mixture was allowed to stand for 1.5 hours at room temperature. The amount of 20-HETE production was measured by using a high performance liquid chromatography having a detector for radioactive substances (supplied by Gilson), equipped with an ODS column (Biocyl C18, supplied by Bio-rad).

Setting an amount of 20-HETE production to 100% when no subject compound was added, the inhibition rate (%) was calculated from the amount of 20-HETE production when a subject compound was added. The results thereof are also shown in the Table described above.

In addition, setting an amount of 20-HETE production to 100% when no subject compound was added, the concentration of the subject compound at which the production of the 20-HETE was inhibited to 50% when the subject compound is added ($IC_{50}$ value) was also calculated. The results thereof are also shown in the Table described above.

INDUSTRIAL APPLICABILITY

The compounds and the pharmaceutically acceptable salts thereof according to the present invention exhibit inhibitory activity on production of 20-HETE, and therefore, they are useful as therapeutic agents for diseases in human subjects and animals, which 20-HETE participates in, such as various kidney diseases, cerebrovascular diseases, or various circulatory diseases.

What is claimed is:

1. A hydroxyformamidine compound represented by the formula:

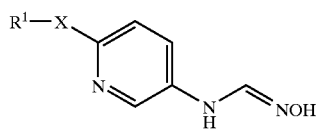

wherein $R^1$ is a group represented by the formula: $R^2$—$(CH_2)_m$— (wherein $R^2$ is a $C_{3-8}$ cycloalkyl group, a $C_{2-6}$ alkoxycarbonyl group, a $C_{2-10}$ alkenyl group, a $C_{2-6}$ alkynyl group, a substituted or non-substituted aryl group, a furyl group, an oxolanyl group, a substituted or non-substituted dioxolanyl group, an oxanyl group, a substituted or non-substituted dioxanyl group, a benzodioxanyl group, a piperidyl group, an N—($C_{1-6}$ alkyl)piperidyl group, a substituted or non-substituted pyridyl group, a thienyl group, a substituted or non-substituted thiazolyl group, or a bicyclo [2.2.1]heptanyl group, and m is an integer of 1 to 8), a group represented by the formula: $R^3$—A— (wherein $R^3$ is a hydrogen atom, a $C_{1-6}$ alkoxy group, a $C_{3-8}$ cycloalkoxy group, a di($C_{1-6}$ alkyl)amino group, a substituted or non-substituted arylamino group, a $C_{1-6}$ alkyl (substituted or non-substituted aryl)amino group, a $C_{1-6}$ alkylthio group, a $C_{1-6}$ alkoxy $C_{1-6}$ alkoxy group, a di($C_{1-6}$alkyl)amino $C_{1-6}$ alkoxy group, a hydroxy group, an acetoxy group, an arylthio group, an aryloxy group, a phthalimidoyl group, a piperidino group, a pyridylthio group, a pyrrolidinyl group, a pyrrolyl group, a morpholino group, or a substituted or non-substituted 2,6-purindion-7-yl group, and A is a straight-chain $C_{2-10}$ alkylene group which may be substituted with a $C_{1-6}$ alkyl group or a trifluoromethyl group), or a $C_{3-8}$ cycloalkyl group, and X is an oxygen atom or a sulfur atom, or a pharmaceutically acceptable salt thereof.

2. The hydroxyformamidine compound or the pharmaceutically acceptable salt thereof, according to claim 1, wherein X is an oxygen atom.

3. The hydroxyformamidine compound or the pharmaceutically acceptable salt thereof, according to claim 1, wherein X is an oxygen atom, and $R^1$ is a group represented by the formula: $R^4$—B— (wherein $R^4$ is a di($C_{1-6}$ alkyl) amino group, a di($C_{1-6}$ alkyl)amino $C_{1-6}$ alkoxy group, a piperidino group, a pyrrolidinyl group, or a morpholino group, and B is a straight-chain $C_{2-6}$ alkylene group which may be substituted with one or two methyl groups).

4. A pharmaceutical composition comprising the hydroxyformamidine compound or the pharmaceutically acceptable salt thereof according to any one of claims 1 to 3 as an active ingredient and a pharmaceutically acceptable carrier.

5. An inhibitor for production of 20-hydroxyeicosatetraenoic acid, comprising the hydroxyformamidine compound or the pharmaceutically acceptable salt thereof according to any one of claims 1 to 3 as an active ingredient.

6. A therapeutic method for treatment of kidney diseases, cerebrovascular diseases, or circulatory diseases, comprising administering to a patient an effective amount of the hydroxyformamidine compound or the pharmaceutically acceptable salt thereof according to any one of claims 1 to 3.

7. A method for inhibiting production of 20-hydroxyeicosatetraenoic acid, comprising administering to a patient in need thereof an effective amount of the hydroxyformamidine compound or the pharmaceutically acceptable salt thereof according to any one of claims 1 to 3.

* * * * *